(12) United States Patent
Hammerschmidt et al.

(10) Patent No.: US 10,201,165 B2
(45) Date of Patent: Feb. 12, 2019

(54) **FORMULATIONS AND METHODS FOR ANTIFUNGAL ACTIVITY FROM *PRUNUS MAACKII* PERIDERM**

(71) Applicant: Board of Trustees of Michigan State University, East Lansing, MI (US)

(72) Inventors: Raymond Hammerschmidt, East Lansing, MI (US); Linzi Kaniszewski, Midland, MI (US); Cory Outwater, Grawn, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/502,553

(22) PCT Filed: Aug. 7, 2015

(86) PCT No.: PCT/US2015/044175
§ 371 (c)(1),
(2) Date: Feb. 8, 2017

(87) PCT Pub. No.: WO2016/022901
PCT Pub. Date: Feb. 11, 2016

(65) Prior Publication Data
US 2017/0238558 A1      Aug. 24, 2017

Related U.S. Application Data

(60) Provisional application No. 62/035,070, filed on Aug. 8, 2014.

(51) Int. Cl.
*A61K 36/736* (2006.01)
*A01N 65/34* (2009.01)
*A01N 65/00* (2009.01)
*A01N 43/16* (2006.01)

(52) U.S. Cl.
CPC .............. *A01N 65/34* (2013.01); *A01N 43/16* (2013.01); *A01N 65/00* (2013.01); *A61K 36/736* (2013.01); *Y02A 50/351* (2018.01); *Y02A 50/354* (2018.01)

(58) Field of Classification Search
None
See application file for complete search history.

(56) References Cited

U.S. PATENT DOCUMENTS

| 2004/0105901 A1 | 6/2004 | Roberts |
| 2009/0269425 A1 | 10/2009 | Truscott et al. |
| 2013/0243708 A1 | 9/2013 | Florence et al. |

FOREIGN PATENT DOCUMENTS

WO    2011099025 A1    8/2011

OTHER PUBLICATIONS

Revilla et al. (1998) J. Agric. Food Chem. 46, 4592-4597. (Year: 1998).*
Raskin et al. (2004) Current Pharmaceutical Design, 10, 3419-3429. (Year: 2004).*
McNulty, et al., "Isolation of flavonoids from the heartwood and resin of Prunus avium and some preliminary biological investigations", Abstract, (2009), 2 pages, last accessed on Mar. 13, 2017.
Board of Trustees of Michigan State University, PCT/US2015/044175 filed Aug. 7, 2015, "International Preliminary Report on Patentability", dated Feb. 23, 2017 and "Written Opinion of the International Searching Authority", dated Nov. 9, 2015 , 7 pages.

* cited by examiner

*Primary Examiner* — Christopher R Tate
*Assistant Examiner* — Russell G Fiebig
(74) *Attorney, Agent, or Firm* — McKee, Voorhees & Sease, PLC

(57) ABSTRACT

The present invention describes methods and formulations for protecting plants against various pathogens, involving the use of *Prunus maackii* materials. In some embodiments the biopesticide formulation comprises of at least one flavonoid such as 3,5,7-trihydroxy-6-methoxyflavone, 3,5,7-trihydroxy-6-methoxyflavanone or 5,7-dihydroxy-8-methoxyflavanone. The invention further provides a method of making the biopesticide by extracting a *Prunus* species with a solvent and formulating the composition using adjuvants, and kits for application of the biopesticide.

5 Claims, 27 Drawing Sheets

FIG. 13

FORMULATIONS AND METHODS FOR ANTIFUNGAL ACTIVITY FROM *PRUNUS MAACKII* PERIDERM

RELATED APPLICATIONS

This application claims priority to U.S. Provisional Application Ser. No. 62/035,070 filed under 35 U.S.C. § 111(b) on Aug. 8, 2014, the disclosure of which is incorporated herein by reference in its entirety.

STATEMENT REGARDING FEDERALLY SPONSORED RESEARCH

This invention was made with government support under 2009-34469-19931 and 2010-34469-20997 awarded by the U.S. Department of Agriculture. The government has certain rights in the invention.

BACKGROUND OF THE INVENTION

Plants are subject to attack by a great number of pests such as fungi, bacteria, and nematodes. As a result, pesticides have been used to protect crops since before 2000 BC. Historically, elemental sulfur, arsenic, mercury, and lead were applied to crops to kill pests. The $17^{th}$ through $19^{th}$ centuries saw the development and use of several natural pesticides (biopesticides), including nicotine sulfate, extracted from tobacco leaves, pyrethrum, derived from chrysanthemums, and rotenone, extracted from the seeds and stems of several plants, such as the jicama vine plant, and the roots of several members of the family Fabaceae. Until the 1940s, arsenic-based pesticides were most commonly used. Beginning that decade, manufacturers began producing synthetic pesticides in large quantities, and their use became widespread. Since 1950, pesticide use has increased over 50-fold, with over 5 billion pounds of pesticide active ingredients being used globally each year.

A primary benefit of pesticide use is controlling pests and plant disease vectors. The use of pesticides has vastly improved agricultural productivity, increasing the global food supply. One study found that not using pesticides reduced crop yields by nearly 10%. Another study found that a ban on pesticides in the United States may result in the rise of food prices, a loss of jobs, and an increase in world hunger levels.

Despite their utility, pesticides have garnered significant attention due to their adverse health and environmental effects. Exposure to pesticides has been linked to a variety of adverse health effects, from irritation of the skin and eyes to more severe effects such as neurological damage, reproductive issues, and cancers such non-Hodgkin lymphoma and leukemia. Studies have also linked pesticide exposure to the development of neurological disorders, birth defects, fetal death, and neurodevelopmental disorders, among other diseases and disorders.

Pesticide use has also been shown to have negative environmental effects. Over 98% of sprayed insecticides and 95% of herbicides reach a destination other than their target species. This pesticide drift results in water pollution and soil contamination. Pesticide use has also been shown to contribute to pollinator decline, destruction of habitats, reduced biodiversity and nitrogen fixation, and to threaten endangered species. Furthermore, chlorinated hydrocarbon pesticides are not excreted, but rather dissolve in fats. This results in organisms tending to retain such pesticides indefinitely, resulting in biological magnification, where the chlorinated hydrocarbons are increasingly concentrated at each level moving up the food chain.

With increased environmental and health concerns related to pesticide use, and increased resistance of pathogens and pests to chemical control materials, new chemistries that are effective, environmentally safe, and non-toxic to humans are needed.

Plants have evolved highly effective mechanisms for resistance to pests. When a plant is discovered to produce one or more substances capable of controlling pests, an extract or isolated compound from the plant may be utilized as a biopesticide. Biopesticides are typically either microbial or biochemical in nature, and may have a broad range of pest control capabilities including herbicidal, insecticidal, nematicidal, termiticidal, bactericidal, antimicrobial, and fungicidal properties. Microbial biopesticides include entomopathogenic fungi, *Trichoderma* species, *Ampelomyces quisqualis*, *Bacillus subtilis*, beneficial nematodes, and entomopathogenic viruses. Various materials, including fungal and plant extracts, have also been described as biopesticides, including plant-derived products such as alkaloids, terpenoids, phenolics and other secondary chemicals, and certain vegetable oils such as canola oil.

Biopesticides may be applied in a manner similar to conventional chemical pesticides, and have already established themselves on a variety of crops. Unfortunately, many biopesticides are highly specific, requiring an exact identification of the target pest and/or pathogen. Biopesticides also vary considerably in efficacy.

Currently, biopesticides account for only about 3% of the total pesticide market, with a value of $750M (2008). There is a need to develop safer and more sustainable pesticides that are efficient and have a broad spectrum of use. Further, there is a need for sustainable pesticides that can be utilized in both the organic and conventional markets.

SUMMARY OF THE INVENTION

Provided herein is a method of protecting a plant from a pathogen. The method involves applying an effective amount of a *Prunus maackii* crude extract to a plant and protecting the plant from a pathogen. In certain embodiments, the pathogen is selected from the group consisting of an Ascomycete plant pathogen, a Basidiomycete plant pathogen, and an Oomycete plant pathogen. In certain embodiments, the pathogen is a fungus or a fungus-like microorganism. In particular embodiments, the fungus or fungus-like microorganism is selected from the group consisting of: *Sclerotinia sclerotiorum*; *Armillaria ostoyae*; other *Armillaria* spp. *Alternaria solani*; *Colletotrichum orbiculare*; *Cladosporium cucumerinum*; *Cochliobolus carbonum*; *Fusarium sambucinum*; and TBZ-resistant *F. sambucinum*.

In certain embodiments, the *Prunus maackii* extract comprises 3,5,7-trihydroxy-6-methoxyflavone, 3,5,7-trihydroxy-6-methoxyflavanone, or 5,7-dihydroxy-8-methoxyflavanone. In certain embodiments, the extract is formulated as an aqueous solution further comprising one or more adjuvants. In certain embodiments, the extract is prepared by acetone extraction, hot water extraction, methanol extraction, or autoclave extraction.

Further provided is a biopesticide formulation comprising a non-toxic amount of *Prunus maackii* extract, and one or more adjuvants. In certain embodiments, the one or more adjuvants are selected from the group consisting of: surfactants; emulsifiers; thickening agents; spreaders; stickers; oils; penetrants; and wetting agents. In particular embodiments, the formulation further comprises a synthetically produced flavonoid selected from the group consisting of 3,5,7-trihydroxy-6-methoxyflavone, 3,5,7-trihydroxy-6-methoxyflavanone, and 5,7-dihydroxy-8-methoxyflavanone. In particular embodiments, the extract is prepared by acetone extraction, hot water extraction, or autoclave extraction.

Further provided is a method of making a biopesticide comprising the steps of extracting plant tissue of *Prunus maackii* with a solvent to form a crude extract, and mixing a non-toxic amount of the crude extract with one or more adjuvants to produce a biopesticide. In certain embodiments, the solvent is selected from the group consisting of acetone, methanol, ethanol, water, ethyl acetate, ether, chloroform, and mixtures thereof. In certain embodiments, the extracting comprising placing macerated *Prunus maackii* periderm tissue in the solvent and allowing the periderm tissue to extract for a period of time; concentrating the extract by rotary evaporation to produce crystals; and drying the crystals by lyophilization. In particular embodiments, the period of time is about three days.

Further provided is a method of making a biopesticide comprising the steps of extracting crude extract from *Prunus maackii*; mixing a non-toxic amount of the crude extract with one or more adjuvants; and formulating the mixture into a powder, liquid, spray, or briquette.

Further provided is a biopesticide formulation comprising a non-toxic amount of at least one flavonoid selected from the group consisting of 3,5,7-trihydroxy-6-methoxyflavone, 3,5,7-trihydroxy-6-methoxyflavanone, and 5,7-dihydroxy-8-methoxyflavanone, wherein the flavonoid is extracted from plant materials; and one or more adjuvants.

Further provided is a pesticide composition comprising a mixture of *Prunus maackii* extract and one or more pesticides selected from the group consisting of: a *Eucalyptus* formulation; a *Callistemon* formulation; a *Bacillus thuringiensis-Kurstakii* insecticide or larvicide; a *Beauveria bassiana* insecticide; a *Metarhizium anisoplae* insecticide; a *Verticillium lecanii* insecticides; a *Spodoptera* Nucleopolyhedrovirus insecticide; a *Pseudomonas fluorescens* fungicide; a *Tricoderma viridae* fungicide; a *Paceliomyce*-based nematicide; a *Trichoderma harzianum* fungicide; a HaNPV-based insecticide; an amino acid-type herbicide; Carbendazim; Mancozeb; Ridomil; Dithane M-45; Chlorothalanil; Propaconazole; Spinosad; Novaluron; Indoxacarb; Thiomethoxam; Actamiprid; Imidocloprid; Chlorpyriphos; Avermectin; 2;4-dichlorophenoxy acetic acid; acephate; acetamiprid; alachlor; allethrin; alphacypermethrin; alphanaphthyl acetic acid; aluminium phosphide; anilophos; atrazine; aureofungin; azadirachtin; azoxystrobin; *bacillus thuringiensis; bacillus thuringiensis*; barium carbonate; *beauveria bassiana*; bendiocarh; benlbracarb; benomyl; bensulfuron; beta cyfluthrin; bifenazate; bifenthrin; bitertanol; bromadiolone; buprofezin; butachlor; captan; carbaryl; carbofuran; carhosulfan; carboxin; carfentazone ethyl; carpropamid; cartap hydrochloride; chlorofenvinphos; chlorfenapyr chlorinturon ethyl; chlormequat chloride (ccc); chlorothalonil; chlorpyriphos; chlorpyriphos methyl; cinmethylene; clodinafop-propargyt (pyroxofop-propargyl); clomazone chlothianidi; copper hydroxide; copper oxychloride; copper sulfate; couinachlor; coumatetmlyl; cuprous oxide; cyfluthrin; cyhalolop-butyl; cymoxanil; cypeimethrin; cyphenothrin; dazomet; deltamethrin (decamethrin); diazinon; dichloro-diphenyl-trichloroethane; a dichloropropene and dichloropropane mixture; diclorvos; diclofop-methyl; dicofol; difenocenazole; difenthiuron; diflubenzuron; dimethoate; dimethomorph; dinocap; dithianon; diuron; dodine; d-trans allethrin; edifenphos; emamectin benzoate; endosulfan; ethephon; ethion; ethofenprox (etofenprox); ethoxysulfuron; an ethylene dibromide and carbon tetrachloride mixture; fenamidone; fenarimol; fenazaquin; fenitrothion; fenobucarb (bpmc); fenoxaprop-p-ethyl; fenpropathrin; fenpyroximate; fenthion; fenvalerate; fipronil; flubendiamide; fluchloratin; ftufenacet; flufenoxuron; flufenzine; flusilazole; fluvalinate; forchlorfenuron; fosetyl-al; gibberellic acid; glufosinate ammonium; glyphosate; hexaconazole; hexazinone; hexythiazox; hydrogen cyanamid; imazethapyr; imidacloprid; iniiprothrin; indoxacarb; iprobenfos (kitazin); iprodione; isoprothiolane; isoproturon; kasugamycin; larnbdacyhalothrin; lime sulphur; lindane; linuron; lufenuroin; magnesium phosphide plates; malathion; mancozeb; mepiquate chloride; mesosullbron methyl and iodosulfuron methyl sodium; metalaxyl; metalaxyl-m; metaldehyde; methabenzthiazuron; methornyl; methoxy ethyl mercury chloride; methyl bromide; methyl chlorophenoxy acetic acid; methyl parathion; metiram; metolachlor; metribuzin; metsulfuron methyl; milbemectin; monocrotophos; myclobutanil; novaluron; nuclear polyhyderosis virus of *helicoverpa armigera*; nuclear polyhyderosis virus of *spodoptera litura*; oxadiargyl; oxadiazon; oxycarboxin; oxydemeton-methyl; oxyfluorfen; paclobutrazole; paraquat dichloride; penconazole; pencycuron; pendimethalin; permethrin; phenthoate; phorate; phosalone; phosphamidon; prallethrin; pretilachlor; primiphos-methyl; profenophos; propanil; propergite; propetamphos; propiconazole; propineb; propoxur; pyrachlostrobin; pyrethrins (pyrethrum); pyridalyl; pyriproxyfen; pyrithiobac sodium; quinalphos; quizalofop ethyl; quizalofop-p-tefuryl; s-bioallethrin; sirmate; sodium cyanide; spinosad; streptomycin and tetracycline; sulfosulfuron; sulphur; tebuconazole; temephos; thiacloprid; thifluzamide; thiobencarb (benthiocarb); thiodicarb; thiomethoxain; thiometon; thiophanate-methyl; thiram; transfluthrin; triacontanol; triadimefon; triallate; triazophos; trichlorofon; *trichoderma viride*; tricyclazole; tridemorph; trifluralin; validamycin; *verticillium lecanii*; zinc phosphide; zineb; and zram. In certain embodiments; the composition is fungicide and the one or more pesticides are selected from the group consisting of a *Pseudomonas fluorescens* fungicide; a *Tricoderma viridae* fungicide; a *Trichoderma harzianum* fungicide; Carbendazim; Mancozeb; Ridomil; Dithane M-45; Chlorothalanil; and Propaconazole.

Further provided is a method of treating a plant for a pathogenic disease, the method comprising the steps of applying an effective amount of *Prunus maackii* extract to a plant in need thereof, and treating the plant for a pathogenic disease, wherein the disease is selected from the group consisting of: early blight; *Fusarium* dry rot; *phytophthora* blight of cucurbits; white mold; Northern leaf spot; and *Rhizoctonia* disease. In certain embodiments, the plant is a cucurbit, corn, tomato, eggplant, or pepper plant.

Further provided is a method for reducing the risk of soil-borne diseases, the method comprising the steps of chipping twigs or branches of a *Prunus maackii* tree into a mulch, and applying the mulch to soil to reduce the risk of soil-borne diseases.

Further provided is a kit for preparing a biopesticide formulation comprising a first container housing a *Prunus maackii* extract; and a second container housing one or more adjuvants. In certain embodiments, the kit further comprises a spray bottle.

BRIEF DESCRIPTION OF THE DRAWING

The patent or application file may contain one or more drawings and/or photographs that are best viewed in color.

FIG. 13: Graph showing results of concentration gradient evaluation of *Prunus maackii* periderm for the identification of the antimicrobial threshold.

FIG. 16A shows the growth of *Cladosporium cucumerinum*. FIG. 16B shows the growth of *Sclerotinia sclerotiorum*. FIG. 16C shows the growth of *Collectotrichum orbiculare*. FIG. 16D shows the growth of *Alternaria solani*. FIG. 16E shows the growth of *Botrytis cinerea*. FIG. 16F shows the growth of *Cochliobolus carbonum*. FIG. 16G shows the growth of *Rhizoctonia solani*. FIG. 16H shows the growth of *Fusarium sambucinum*. FIG. 16I shows the growth of TBZ-resistant *F. sambucinum*. FIG. 16J shows the growth of *Phytophthora capsici*.

DETAILED DESCRIPTION OF THE INVENTION

Figure 1:
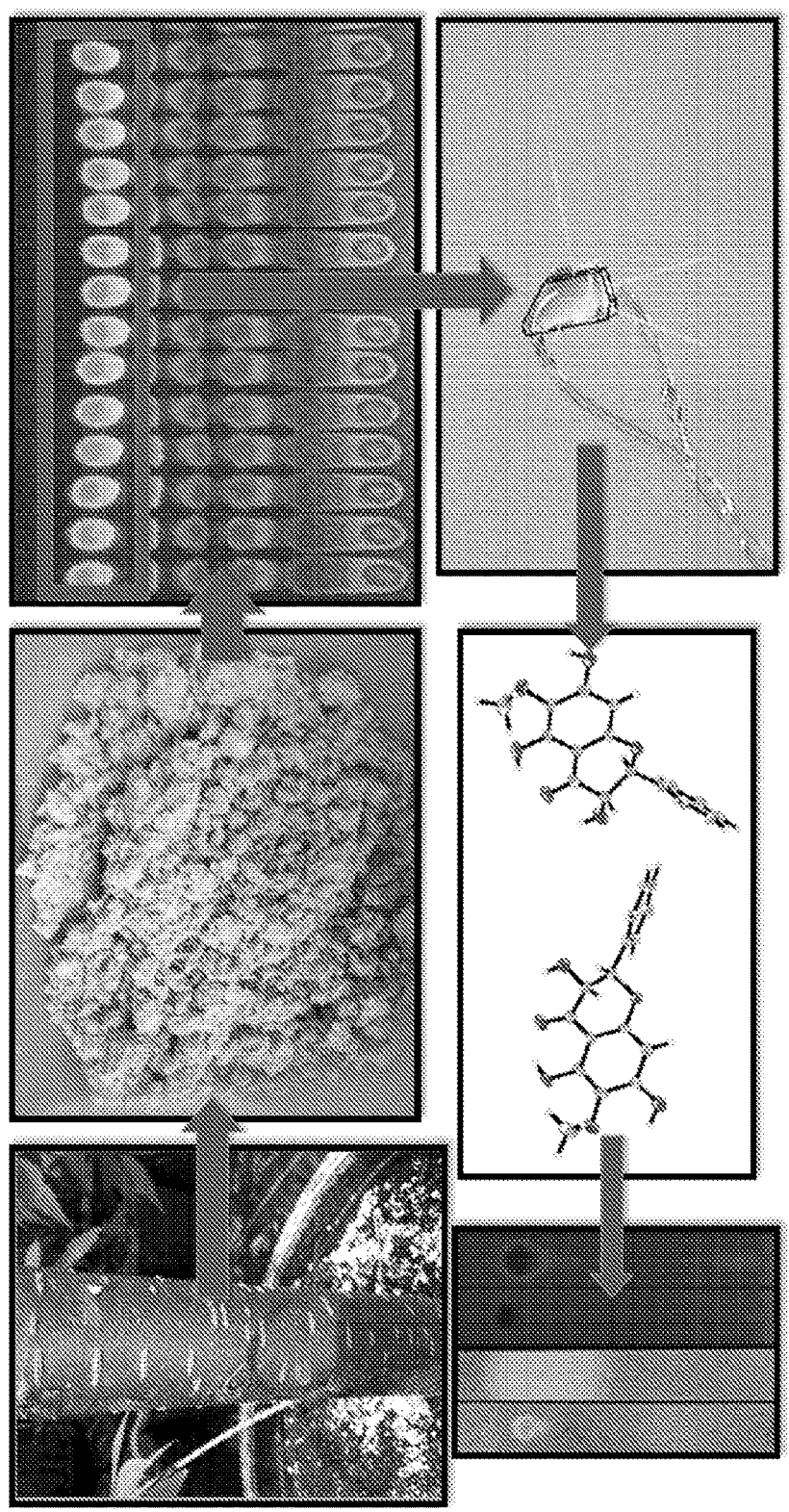
FIG. 1: Illustration depicting a non-limiting process of isolating, concentrating, identifying, and characterizing 2 flavonoids. In one example, 30 grams of periderm tissue were used to collect approximately 7 grams of crude extract. 2 grams of this was crystallized product (unique to *P. maackii*). Compounds were semipurified by preparative thin layer chromatography, and were subjected to crystallization. After the structures were identified, the isolated compounds were re-chromatographed and subjected to bioassays.

Throughout this disclosure, various publications, patents and published patent specifications are referenced by an identifying citation. The disclosures of these publications, patents and published patent specifications are hereby incorporated by reference into the present disclosure in their entirety to more fully describe the state of the art to which this invention pertains.

Unless stereochemistry is specifically indicated, all stereoisomers of the compounds herein are included, as pure compounds as well as mixtures thereof.

It will be appreciated by one of ordinary skill in the art that asymmetric centers may exist in any of the compounds described herein. Thus, the compounds may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

It will be appreciated that any compound described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

As used herein, the term "substituted" includes all permissible substituents of organic compounds. In a broad aspect, the permissible substituents include acyclic and cyclic, branched and unbranched, carbocyclic and heterocyclic, aromatic and nonaromatic substituents of organic compounds. For purposes of explanation, heteroatoms such as nitrogen may have hydrogen substituents and/or any permissible substituents of organic compounds described herein which satisfy the valencies of the heteroatoms. Furthermore, there is not any intention to be limited in any manner by the permissible substituents of organic compounds. Combinations of substituents and variables envisioned are preferably those that result in the formation of stable compounds useful in the inhibition of growth of various plant pathogens such as fungus or fungus-like microorganisms.

General Description

The *Prunus maackii*, also known as the amur cherry or amur chokecherry, is a species of cherry tree indigenous to parts of Korea, Siberia, and Manchuria. Provided herein are materials, methods, and formulations involving the use of *Prunus maackii* plant products that have broad-spectrum activity against a variety of plant pathogens, including fungal species *Armillaria ostoyae* (also known as *Armillaria solidipes*). The diseases caused by *Armillaria ostoyae* significantly restrain the production of *Prunus* and many other woody species. Several other *Armillaria* species are also serious pathogens, but there are no existing, consistent control measures for this genus of pathogen. In accordance with the present disclosure, *Prunus maackii* contains broad-spetrum, pre-formed antimicrobial compounds.

Diseases caused by fungal species are considered among the most widespread and damaging of plants worldwide, creating a special need for fungicides. Some natural antifungal chemistries from plants have been identified, though few have been developed into disease management products. In accordance with the present disclosure, a crude extract of the outer bark (periderm) or tissues of *Prunus maackii* unexpectedly possesses significant growth inhibition activity against a range of fungi and fungus-like microorganisms. Different parts of the *Prunus maackii* tree possess different and useful antimicrobial activity. Furthermore, the effect was observed in autoclaved media containing periderm or other plant parts, indicating the presence of pre-formed, heat-stable antimicrobial compounds. Thus, provided herein are plant-based methods and formulations for broad-spectrum plant protection.

*P. maackii* periderm naturally exfoliates, meaning the plant provides a sustainable source of raw material; the bark can be collected as it naturally peels away from the trunk and branches. The crude extract can be optionally purified, or can be used in its raw form for plant protection. The extract can be combined with any suitable combination of adjuvants or additives, as discussed in detail below, in a biopesticide formulation.

The use of *Prunus maackii* in a biopesticide formulation is advantageous because of the high concentration of antifungal compounds, ease of extraction, an ability to inhibit a wide range of fungi, and suitability for a variety of uses other than plant protection. *P. maackii* inhibits the growth of fungi and microorganisms such as, but not limited to, Ascomycete, Basidiomycete, and Oomycete plant pathogens. Furthermore, *Prunus maackii* periderm is not phytotoxic—in particular to cucumber and tomato plants—making it especially suitable for formulation as a biofungicide. Alternatively, *P. maackii* extract is suitable for enhancing the biofungicidal activity of an antimicrobial agent.

Figure 18A:
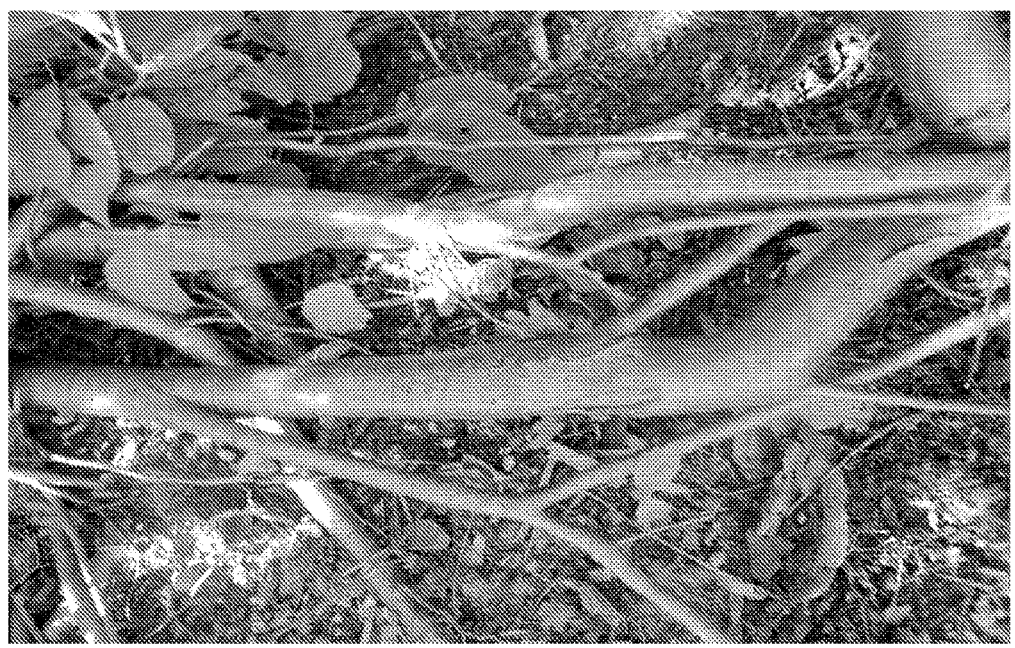
FIG. 18A: Photograph of *Prunus maackii* shoots and roots used for woody mulch-amended medium.
Figure 18B:
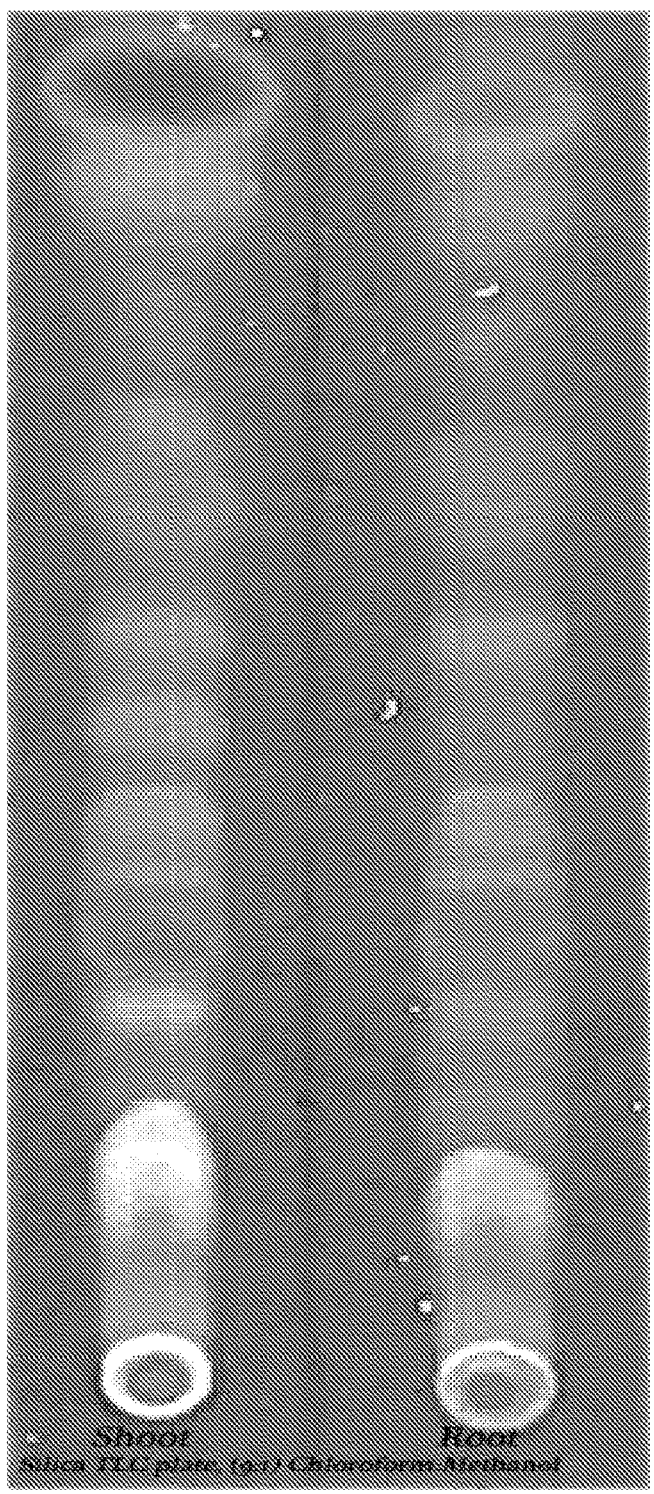
FIG. 18B: Silica TLC plate showing the presence of active compound in extracts from both the shoot (left) and the root (right) of *Prunus maackii*.

Furthermore, the entire *Prunus maackii* tree can be utilized. As shown in the examples herein, multiple types of tissues from *P. maackii* inhibit growth of several fungal species. In particular embodiments of the methods and formulations described herein, the periderm of *P. maackii* is used. The periderm is the protecting outer layers of the bark of the plant. The compounds believed responsible for the growth-inhibiting activity are present in both the root periderm and the shoot periderm of the *Prunus maackii* plant. (FIG. 18B.) In particular embodiments, the cambium of *P. maackii* is used. The cambium is a tissue layer in the vascular tissue of the plant responsible for secondary growth.

Crude extract can be produced from *P. maackii* material through any of several methods. Generally, *P. maackii* material is extracted with at least one solvent selected from the group consisting of water; a C1-C4 lower alcohol such as methanol, ethanol, and the like; acetone; ethyl acetate; ether; chloroform; and mixtures thereof. The extraction can be performed in an autoclave using water because the active compounds in the extract are heat-stable. The extract can be concentrated by, for example, rotary evaporation, which may cause crystallization. The crystal products can then be filtered out, and optionally dried through a suitable method such as lyophilization. The antifungal activity of this crude extract from *P. maackii* is stronger on a weight basis than many other antifungal extracts from plant materials. By way of a non-limiting example, medium containing about 1.2% of *P. maackii* crude extract has effective growth-inhibiting activity, while other natural fungicides require concentrations of about 20%.

A polar solvent-soluble extract can be prepared by fractionating the above-described crude extract with a polar solvent such as, but not limited to: water; a C1-C4 lower alcohol such as methanol, ethanol, or butanol; or a mixture thereof. A non-polar solvent soluble extract can be prepared by extracting the above-described crude extract with a non-polar solvent such as, but not limited to: ethyl acetate; hexane; chloroform; methylene chloride; and mixtures thereof.

Other extracts can be produced through more complex methods. In one non-limiting example, macerated *P. maackii* material is introduced with a solvent into a container and allowed to extract. Alternatively, *P. maackii* material is macerated to produce a macerated slurry or solution. The macerated material is distilled in order to condense volatile compounds, which are collected as a concentrated extract. In another non-limiting example, extract can be produced from periderm or cambium tissues by drying them, grinding them into a powder, suspending the powder in a suitable solvent to form a solution, heating and cooling the solution, and filtering the solution to produce an extract filtrate. Optionally, the filtrate can be concentrated to produce a residue.

There is strong antifungal activity against *A. ostoyae* when periderm from *P. maackii* is incorporated into culture media, but not when periderm from other *Prunus* plants are similarly incorporated. The extract of *P. maackii* is also effective against many other pathogens such as, but not limited to: *Sclerotinia sclerotiorum; Alternaria Solani; Colletotrichum orbiculare; Cladosporium cucumerinum; Cochliobolus carbonum; Fusarium sambucinum*; and TBZ-resistant *F. sambucinum*. *P. maackii* extract is rich in certain phenolic compounds, which are organic compounds that have a hydroxyl group bonded directly to an aromatic hydrocarbon group. Without being bound by any particular theory, it is believed the antifungal activity of *P. maackii* periderm is due at least in part from the presence of the antifungal phenolic compounds 3,5,7-trihydroxy-6-methoxyflavone (Alnusin) and 3,5,7-trihydroxy-6-methoxyflavanone (Alnustinol). These compounds, which are flavonoids, have the following chemical structures, denoted Formula I and Formula II, respectively:

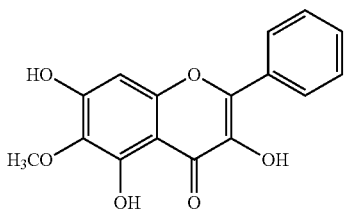

Formula I

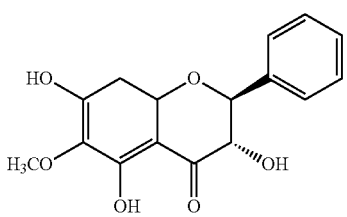

Formula II

There is also a stereoisomer of Alnustinol present in *Prunus maackii*, along with a compound known as dihydrowogonin (5,7-dihydroxy-8-methoxy-2-phenyl-2,3-dihydrochromen-4-one; also known as 5,7-dihydroxy-8-methoxyflavanone). Dihydrowogonin has the chemical structure of Formula III:

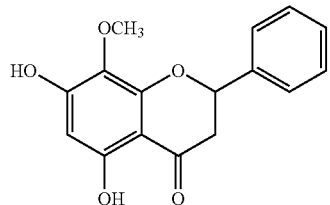

Formula III

The presence of compounds of formulas I and II was confirmed by thin layer chromatography bioassays. The presence of a compound of formula III was determined by x-ray crystallography. The compounds I and II were identified as flavonoids by high performance liquid chromatography coupled with UV or mass spectroscopy, and the structures of the compounds were confirmed by X-ray crystallography. Similar bioassays of the periderm from other *Prunus* plants resulted in either no detection, or detection at very low concentrations, of these compounds. Surprisingly, it was determined that flavonoids of formulas I, II, and III are formed in *Prunus maackii* from cinnamoyl-coenzyme A, as compared to most flavonoids, including others in *Prunus* spp., that are derived from p-coumaroyl CoA, as is common for most plants.

Thus, provided herein are formulations comprising *P. maackii* extract and/or synthetically produced flavonoids such as 3,5,7-trihydroxy-6-methoxyflavone, 3,5,7-trihydroxy-6-methoxyflavanone, 5,7-dihydroxy-8-methoxyflavanone, and derivatives thereof. Suitable derivatives include, but are not limited to, glycosylated flavanones. The formulations are suitable as biopesticides to provide protection against a wide range of plant pathogens. As described below, such a formulation may further include one or more adjuvants, and/or one or more other flavonoids. Synthetic flavones can be produced through any of several suitable methods, such as an Allan-Robinson reaction, an Auwers synthesis, a Baker-Venkataraman rearrangement, an Algar-Flynn-Oyamada reaction, the dehydrative cyclization of various 1,3-diaryl diketones, or a Wessely-Moser rearrangement. Flavones also have beneficial effects against various diseases such as certain cancers, diabetes mellitus, osteoporosis, and atherosclerosis. Synthetic flavonoids can be produced through any of several methods, such as a polyketide pathway.

Biopesticide Formulations

Provided herein are biopesticide formulations containing *P. maackii* extract or other materials, which provide anti-pathogen activity. In certain embodiments, the biopesticide formulations provide strong antifungal activity. Such a formulation contains non-toxic amounts of the active ingredient *P. maackii* and one or more adjuvants or additives such as, but not limited to: surfactants; wetting agents; thickening agents; spreaders; stickers; oils; anti-foaming materials; buffering agents; compatibility agents; nutrients; fertilizers; and growth enhancing agents. The non-toxic amount of the active ingredient is understood to mean an amount that is non-toxic to humans. Those skilled in the art will recognize that suitable combinations and amounts of adjuvants and/or additives are those which do not cause damage to the target plant(s). In certain embodiments, the formulations contain less than 1% by weight *P. maackii* extract. In certain embodiments, the formulations contain about 1% by weight *P. maackii* extract. In certain embodiments, the formulations contain about 5% by weight *P. maackii* extract. In certain embodiments, the formulations contain about 10% by weight *P. maackii* extract. In certain embodiments, the formulations contain about 20% by weight *P. maackii* extract. In certain embodiments, the formulations contain more than 20% by weight *P. maackii* extract. It is understood that the biopesticide formulations described herein can be formulated as contact pesticides, translaminar pesticides, or systemic pesticides.

Formulations containing *P. maackii* extract are generally aqueous because the extract is water-soluble. The waxy surfaces of plants make it difficult for water-based sprays to penetrate. Therefore, in certain embodiments, the formulations containing *P. maackii* contain one or more surfactants. Surfactants facilitate the emulsifying, dispersing, spreading, wetting, or other surface modifying properties of the aqueous formulation. Surfactants typically have a hydrophilic head and a hydrophobic tail, the structure of which helps to overcome the surface tension of water and allow for the formulation to be more evenly dispersed on the surface of the target. Surfactants may also enhance foaming and other spreading properties. Suitable surfactants include, but are not limited to: anionic surfactants; cationic surfactants; amphoteric surfactants; nonionic surfactants; and blends thereof. Surfactants or blends thereof may be present in the formulation at a concentration ranging from about 0.1% by weight to about 99% weight. In particular embodiments, the surfactants or blends of surfactants are present at about 10% by weight, about 20% by weight, about 30% by weight, about 40% by weight, about 50% by weight, about 60% by weight, about 70% by weight, about 80% by weight, or about 90% by weight of the formulation. The skilled practitioner will recognize that the concentration of surfactant in the formulation will depend on several factors such as the identity of the target plant(s), the identity of the surfactant(s), and the method of application to the target plant(s).

Nonionic surfactants are preferred for horticulture applications because they remain stable and do not cause harm to plants when properly used. Nonionic surfactants can include, but are not limited to: sugar-ester type nonionic surfactants, exemplified by sorbitan fatty acid esters, polyoxyethylenesorbitan fatty acid esters, and sucrose fatty acid esters; fatty acid ester type nonionic surfactants, exemplified by polyoxyethylene fatty acid esters, polyoxyethylene resin acid esters and polyoxyethylene fatty acid diesters; vegetable oil type nonionic surfactants, exemplified by polyoxyethylene castor oil and hydrogenated polyoxyethylene castor oil; alcohol type nonionic surfactants, exemplified by polyoxyelhylenealkyl ethers; alkylphenol type nonionic surfactants, exemplified by polyoxyethylenealkyl phenyl ethers, polyoxyelhylenedialkyl phenyl ethers and polyoxyethylenealkyl phenyl ether-formalin condensates; polyoxyethylene-polyoxyopropylene block polymer type nonionic surfactants, exemplified by polyoxyethylene-polyoxypropylene block polymers, aikylpolyoxyethylene-polyoxypropylene block polymer ethers, and alkylphenylpolyoxyethylene-polyoxypropylene block polymer ethers; bisphenol type nonionic surfactants, exemplified by polyoxybisphenyl ethers; polyaromatic ring type nonionic surfactants, exemplified by polyoxyalkylenebenzyl phenyl ethers and polyoxyalkylenestyryl phenyl ethers; silicone type nonionic surfactants, exemplified by polyoxyethylene ether type silicone surfactants and polyoxyethylene ester type silicone surfactants; fluorine type nonionic surfactants; and combinations thereof.

Anionic surfactants include, but are not limited to: sulfate type anionic surfactants, exemplified by alkyl sulfates, polyoxyethylenealkyl ether sulfates, polyoxyethylenealkyl phenyl ether sulfates, polyoxystyryl phenyl ether sulfates, and polyoxyethylene-polyoxypropylene block polymer sulfates; sulfonate type anionic surfactants, exemplified by paraffinsulfonates, dialkyl sulfosuccinates, alkylbenzenesulfonates, monoalkylnaphthalenesulfonates, dialkylnaphthalenesulfonates, naphthalenesulfonate-formalin condensates, alkyl diphenyl ether disulfonates, ligninsulfonates, and polyoxyethylenealkyl phenyl ether sulfonates; and phosphate type anionic surfactants, exemplified by polyoxyethylenealkyl ether phosphates, polyoxyethylenemonoalkyl phenyl ether phosphates, polyoxyethylenedialkyl phenyl ether phosphates, polyoxyethylenestyryl phenyl ether phosphates, polyoxyethylene-polyoxypropylene block polymer phosphates, and alkylphosphates.

Amphoteric surfactants include, but are not limited to: didecyl ethanolamine oxide; dodecyl dimethylamine oxide; tetradecyl dimethylamine oxide; hexadecyl dimethylamine oxide; octadecyl dimethylamine oxide; coco dimethylamine oxide; coco bis(2-hydroxyethylamine oxide; dicocomethylamine oxide; dicocoethanolamine oxide; cocoylamidopropyl dimethylamine oxide; tallow dimethylamine oxide; tallow diethanolamine oxide; ditallow methylamine oxide; ditallow ethanolamine oxide; di(hydrogenated tallow) methylamine oxide; tallowylamidopropyl dimethylamine oxide; 9-octadecenoyl dimethylamine oxide; N-cocomorpholine N-oxide; coco dimethylbetaine; cocoylamidopropyl dimethyl betaine; lauroylamidopropyl dimethyl betaine; cocoamphocarboxyglycinate; tallow amphopolycarboxyglycinate; N-coco-3-aminobutyric acid; and combinations thereof.

Cationic surfactants include, but are not limited to: secondary, tertiary, or quaternary ammonium compounds in which all amine hydrogens have been replaced by organic radical substitutions; simple ammonium salts containing a long-chain alkyl group which confers hydrophobicity and one or more amine hydrogens; ethoxylated amines; phosphonium compounds; sulfonium compounds; arsonium compounds; heterocyclic materials such as pyridinium, morpholinium, and imidazolinium derivatives; and combinations thereof.

The formulations may include one or more defoamers, or foam-inhibitors. Suitable defoamers include, but are not limited to: fatty acid alkyl ester alkoxylates; organopolysiloxanes such as polydimethylsiloxanes and mixtures thereof with microline or silanized silica; perfluoroalkylphosphonates and perfluoroalkylphosphinates; paraffins; waxes; microcrystalline waxes; mixtures of waxes and microcrystalline waxes with silanized silica; and combinations thereof. Mixtures of different foam inhibitors are particularly useful defoamers, such as those comprising silicone, liquid paraffin, and/or waxes.

The formulations may include one or more wetting agents. Wetting agents break the surface tension of water, similar to surfactants, but rely on different chemistry from surfactants. Suitable wetting agents include, but are not limited to, polyoxyethylene esters, ethoxy sulfates, derivatives of ethoxy sulfates mixed with nonionic surfactants, alcohol ethoxylates, and alcohol propoxylates.

The formulations may include one or more penetrants. Penetrants are used to dissolve or penetrate waxy layers on leaves, which allows other chemical to interface with plant cells. Suitable penetrants can contain petroleum by-products, crop oils, complex alcohols, or other hydrocarbons.

The formulations may include one or more thickeners to make the solution more viscous and heavier. Thickeners can be beneficial by reducing drift, odor, and waste of spray solutions. Suitable thickeners include, but are not limited to, polyacrylamide, polyethylene polymers, polysaccharides, vegetable oils, xanthan gum, cellulose, carboxycellulose, methylcellulose, ethylcellulose, propylcellulose, and bentonites. In particular embodiments, thickeners are present in an amount ranging from about 0.01% by weight to about 5% by weight of the formulation.

The formulations may include one or more emulsifier agents, which prevent coagulation. Emulsifiers help aqueous solutions mix with petroleum-based liquids. Suitable emulsifiers (other than certain surfactants listed above that also act as emulsifiers) include, but are not limited to: carboxylates; sulfates; sulfonates; alcohol ethoxylates; alkyl phenol ethoxylates; fatty acid ethoxylates; sorbitan esters; ethoxylated fats or oils; amine ethoxylates; phosphate esters; ethylene oxide-propylene oxide copolymers; fluorocarbons; silicon polymers; polyalkylene glycol ethers; polyalkoxylated nonyl phenyls; alkoxylated primary alcohols; ethoxylated distryrylphenols; ethoxylated distyrylphenol sulfate; ethoxylated tristyrylphenol phosphate; tristyrylphenol phosphate ester; hydroxylated stearic acid polyalkylene glycol polymers; and combinations thereof.

The formulations may further include one or more spreaders that cause the surface tension of the solution to be reduced in such a manner that it easily spread into a thin film over a surface. Spreaders can increase the efficiency of a pesticide formulation. Suitable spreaders include, but are not limited to, fatty acids, latex, aliphatic alcohols, crop oils, and inorganic oils.

The formulations may also have an adjuvant that helps the formulation stick to the plants after spreading. Stickers are similar to thickening agents or oils in that they cause the solution to adhere to the leaf surface. Stickers can also cause the solution to resist rain, evaporation, and runoff. Suitable stickers include, but are not limited to, emulsified polyethylenes, polymerized resins, fatty acids, and petroleum distillates.

The formulations may further include one or more oils. Oils can be used as suffocates, which cut off the air supply to an insect, or as penetrants, which break apart chitin layers, thereby causing insects to die. Oils can also be used like surfactants, forming a film over a leaf and allowing the formulation to enter the plant. Suitable oils include, but are not limited to: crop oils, which are derived from soybeans or other crops; and inorganic oils, which are derived from petroleum. Oils can also be blended with surfactants.

The formulations may also include one or more modified sugars, such as alkyl polyglucosides, which have surfactant-like properties and can be used as spreaders or stickers. These modified sugars are organic, biodegradable, and environmentally friendly. These modified sugars can be low-foaming or high-foaming, and can be used as wetting agents. Beneficially, such modified sugars have very low potential for phytotoxicity because they are derived from plant sugars. The formulations may include one or more natural surfactants other than, or in addition to, alkylated sugars. Suitable natural surfactants include, but are not limited to, coconut oils, palm oils, castor oils, lanolins, and wheat amino acids.

The formulations may further include one or more organosilicates, which are good surfactants and have significant wetting abilities. Suitable organosilicates include, but are not limited to: methyl silicate; ethyl silicate; methylethyl silicate; methylpropyl silicate; and combinations thereof. Inorganic salts are also suitable surfactants, and include, but are not limited to: salts of sodium; potassium; ammonium; calcium; iron; zinc; and magnesium.

Gas producing disintegrants may be added to the formulations. Suitable gas producing disintegrants include, but are not limited to, effervescing agents such as sodium or potassium bicarbonate with a food grade acid such as citric acid.

The formulations may also contain biocarriers derived from other plant materials. For example, the addition of wheat, corn, or oat materials, particular oat protein, may improve the wetability and coating properties of the formulation. As another example, discrete particles obtained from a residual cell mass remaining after lipids, proteins, and sugars have been removed from crushed or ground oil seeds can serve as a delivery system for a biopesticide formulation. The biopesticide formulation can be mixed with such particles, then processed into powder, flakes, granules, pellets, tablets, or briquettes.

Various other additives are possible. For example, the formulations may further include one or more preservatives, plant nutrients, biosupplements, fertilizers, and the like. Such additives may directly or indirectly benefit plant growth, hardiness, yield, or quality. Examples of suitable biosupplements include, but are not limited to, sea plant extracts, animal manures, animal-derived products, paper processing by-products, and compost material obtained by microbial metabolism. Furthermore, the formulations may be supplemented with one or more synthetically produced flavonoids.

The resulting formulation can be formulated as a spray, dry flowables, water dispersible granules, a powder, a liquid, broadcast granules, suspensions, emulsions, tablets, briquettes, and so forth. When the formulation is a granule, tablet, or briquette, it has good hardness and does not tend to crumble or dust, thereby reducing operator exposure to the biopesticide. However, the formulation can be readily dispersed in water for spray applications, and can be applied using standard machinery.

Even though pathogenic diseases of houseplants grown indoors are uncommon, the biopesticide formulations can also be tailored to accommodate house plants. For example, the formulations can be frozen into biopesticide cubes, with such cubes being placed on the house plants in order to deliver not only a source of water but also a pathogen-inhibiting amount of *Prunus maackii* extract over a desired period of time as the frozen biopesticide cube melts. Such embodiments may include various freezing point modifiers or depressants to ensure freezing of the formulation around the freezing point of water or at a temperature suitable for freezing in a conventional, household freezer. Alternatively, a spray formulation containing *Prunus maackii* extract can be sprayed onto an already-frozen ice cube, which is then applied to the plant, or sprayed directly onto the plant. Particular embodiments of the frozen biopesticide cubes include nutrients and other additives tailored to the needs of house plants.

Though the biopesticide formulations are typically aqueous due to the water-soluble nature of *Prunus maackii* extract, it is to be understood that various suspensions and emulsions are included within the scope of the present disclosure. In non-aqueous formulations, a variety of organic solvents can be used. In various embodiments, the formulations contain one or more commercially available hydrophobic organic solvents such as, but not limited to: Hisol SAS-296 (a mixture of 1-phenyl-1-xylylethane and 1-phenyl-1-ethylphenylethane); Hisol SAS-LH; Shellsol A, AB, E, R, T, or D-70; Cactus Solvent HP-MN (containing 80% of methylnaphthalene); Cactus Solvent HP-DMN (containing 80% of dimethylnaphthalene); Cactus Solvent P-100 (alkylbenzene having 9 to 10 of carbon number); Cactus Solvent P-150 (alkylbenzene); Cactus Solvent P-180 (a mixture of methylnaphthalene and dimethylnaphthalene); Cactus Solvent P-200 (a mixture of methylnaphthalene and dimethylnaphthalene); Cactus Solvent P-220 (a mixture of methylnaphthalene and dimethylnaphthalene); Cactus Solvent PAD-1 (dimethylmonoisopropylnaphthalene); Solvesso 100, 150, or 200 (aromatic hydrocarbons); Suwasol 100 (toluene); Suwasol 200 (xylene); Vinycizer 20 (diisotridecyl phthalate); Vinycizer 40 (diisobutyl adipate); Vinycizer 50 (diisodecyl adipate); Vinycizer 85 (dialkyl phthalate); Vinycizer 105 (didecyl phthalate); Vinycizer 124 (dialkyl phthalate); Excepal O-OL (octyl oleate); Excepal L-OL (lauryl oleate); Excepal OD-OL (octyldodecyl oleate); Toxanon PP-1000 (polyoxypropylene glycol); Nikkol IPA-A (isopropyl myristate); Nikkol IPA-EX (isopropyl myristate); Teclean N-30; Teclean N-32; Teclean N-33; Mineral oil 46P; Pesticidal mineral oil P; Pesticidal oil H; Super oil A; Super oil B; Super oil C; Super oil D; Super oil E; Super oil F; Spindle oil No. 1; Spindle oil No. 2; Mineral oil B; Mineral oil C; Naphthesol M; Isosol 300; Isosol 400; Exxol D80, D110, D130 (a mixture of paraffin and cycloparaffin), or D160 (a mixture of paraffin and cycloparaffin); Isopar E, G, H, or M; Neo-Chiozol (kerosene); IP Solvent 2028 or 2835 (isoparaffin oil); Naplex 38 (naphthene oil); Whitelex 205, 207, 215, 247, 2210, 307, 309, 326, or 335; and combinations thereof.

In certain embodiments, the formulation is suitable for a "tank-mix" method of administration. In such embodiments, the *Prunus maackii* extract and adjuvants are present separately, and are mixed with one another a short time prior to administration or delivery. In the tank-mix method, the *Prunus maackii* extract is present, before mixing, as a formulation in water and/or in an organic solvent, or as a solid formulation. The adjuvants, prior to mixing, are present in solution in water and/or in an organic solvent.

The biopesticide formulations of the present disclosure may be combined with one or more other biopesticide and/or synthetic pesticides. Such combinations can be delivered to a plant simultaneously, optionally as a single pesticide composition, or sequentially. The additional biopesticides or synthetic pesticides can be any one or combination of herbicides, algicides, avicides, bactericides, fungicides, insecticides, miticides, molluscicides, miticides, microbial pesticides, ovicides, nematicides, rodenticides, virucides, antifouling agents, or desiccants.

Non-limiting examples of suitable biopesticides and synthetic pesticides include *Eucalyptus* formulations, *Callistemon* formulations, *Bacillus thuringiensis-Kurstakii* insecticides or larvicides, *Beauveria bassiana* insecticides, *Metarhizium anisoplae* insecticides, *Verticillium lecanii* insecticides, *Paceliomyce*-based nematicides, *Spodoptera* Nucleopolyhedrovirus insecticides, *Pseudomonas fluorescens* fungicides, *Tricoderma viridae* fungicides, *Trichoderma harzianum* fungicides, HaNPV-based insecticides, amino acid-type herbicides, Carbendazim, Mancozeb, Ridomil, Dithane M-45, Chlorothalanil, Propaconazole, Spinosad, Novaluron, Indoxacarb, Thiomethoxam, Actamiprid, Imidocloprid, Chlorpyriphos, Avermectin, 2,4-dichlorophenoxy acetic acid, acephate, acetamiprid, alachlor, allethrin, alphacypermethrin, alphanaphthyl acetic acid, aluminium phosphide, anilophos, atrazine, aureofungin, azadirachtin, azoxystrobin, *bacillus thuringiensis, bacillus thuringiensis*, barium carbonate, *beavreria bassiana*, bendiocarb, benfuracarb, benomyl, bensulfuron, beta cyfluthrin, bifenazate, bifenthrin, bitertanol, bromadiolone, buprofezin, butachlor, captan, carbaryl, carbofuran, carbosulfan, carboxin, carfentazone ethyl, carpropamid, cartap hydrochloride, chlorofenvinphos, chlorfenapyr, chlorimuron ethyl, chlormequat chloride (ccc), chlorothalnil, chlorpyriphos, chlorpyriphos methyl, cinmethylene, clodinafop-propargyl (pyroxofop-propargyl), clomazone chlothianidin, copper hydroxide, copper oxychloride, copper sulfate, coumachlor, coumatetralyl, cuprous oxide, cyfluthrin, cyhalofop-butyl, cymoxanil, cypermethrin, cyphenothrin, dazomet, deltamethrin (decamethrin), diazinon, dichloro-diphenyl-trichloroethane, a dichloropropene and dichloropropane mixture, diclorvos, diclofop-methyl, dicofol, difenocenazole, difenthiuron, diflubenzuron, dimethoate, dimethomorph, dinocap, dithianon, diuron, dodine, d-trans allethrin, edifenphos, emamectin benzoate, endosulfan, ethephon, ethion, ethofenprox (etofenprox), ethoxysulfuron, an ethylene dibromide and carbon tetrachloride mixture, fenamidone, fenarimol, fenazaquin, fenitrothion, fenobucarb (bpmc), fenoxaprop-p-ethyl, fenpropathrin, fenpyroximate, fenthion, fenvalerate, fipronil, flubendiamide, fluchloralin, flufenacet, flufenoxuron, flufenzine, flusilazole, fluvalinate, forchlorfenuron, fosetyl-al, gibberellic acid, glufosinate ammonium, glyphosate, hexaconazole, hexazinone, hexythiazox, hydrogen cyanamid, imazethapyr, imidacloprid, imiprothrin, indoxacarb, iprobenfos (kitazin), iprodione, isoprothiolane, isoproturon, kasugamycin, lambdacyhalothrin, lime sulphur, lindane, linuron, lufenuro/n, magnesium phosphide plates, malathion, mancozeb, mepiquate chloride, mesosulfuron methyl and iodosulfuron methyl sodium, metalaxyl, metalaxyl-m, metaldehyde, methabenzthiazuron, methomyl, methoxy ethyl mercury chloride, methyl bromide, methyl chlorophenoxy acetic acid, methyl parathion, metiram, metolachlor, metribuzin, metsulfuron methyl, milbemectin, monocrotophos, myclobutanil, novaluron, nuclear polyhyderosis virus of *helicoverpa armigera*, nuclear polyhyderosis virus of *spodoptera litura*, oxadiargyl, oxadiazon, oxycarboxin, oxydemeton-methyl, oxyfluorfen, paclobutrazole, paraquat dichloride, penconazole, pencycuron, pendimethalin, permethrin, phenthoate, phorate, phosalone, phosphamidon, prallethrin, pretilachlor, primiphos-methyl, profenophos, propanil, propergite, propetamphos, propiconazole, propineb, propoxur, pyrachlostrobin, pyrethrins (pyrethrum), pyridalyl, pyriproxyfen, pyrithiobac sodium, quinalphos, quizalofop ethyl, quizalofop-p-tefuryl, s-bioallethrin, sirmate, sodium cyanide, spinosad, streptomycin and tetracycline, sulfosulfuron, sulphur, tebuconazole, temephos, thiacloprid, thifluzamide, thiobencarb (benthiocarb), thiodicarb, thiomethoxain, thiometon, thiophanate-methyl, thiram, transfluthrin, triacontanol, triadimefon, triallate, triazophos, trichlorofon, *trichoderma viride*, tricyclazole, tridemorph, trifluralin, validamycin, *verticillium lecanii*, zinc phosphide, zineb, and ziram.

In particular embodiments, the biopesticide formulation or *P. maackii* extract is combined with one or more fungicides selected from *Pseudomonas fluorescens* fungicide, *Tricoderma viridae* fungicide, *Trichoderma harzianum* fungicide, Carbendazim, Mancozeb, Ridomil, Dithane M-45, Chlorothalanil, and Propaconazole for enhanced fungicidal activity.

In particular embodiments, the biopesticide formulation or *P. maackii* extract is combined with a herbicide to provide protection against various pathogens and unwanted plants. Suitable herbicides include, but are not limited to, agriculturally acceptable salts of N-(phosphonomethyl)glycine, DL-homoalanin-4-yl(methyl)phosphinic acid, and 4-[hydroxy(methyl)phosphinoyl]-L-homoalanyl-L-alanyl-L-alanine; 3-isopropyl-1H-2,1,3-benzothiadiazin-4(3H)-one 2,2-dioxide; 3,6-dichloropicolinic acid; (2,4-dichlorophenoxy) acetic acid; 3,6-dichloro-2-methoxybenzoic acid; 2-(2,4-dichlorophenoxy) propionic acid; (4-chloro-2-methylphenoxy) acetic acid; 4-(4-chloro-O-tolyloxy)butyric acid; 2-(4-chloro-2-methylphenoxy)propionic acid; and 4-amino-3,5,6-trichloropicolinic acid.

The formulations described herein are useful for preventing or ameliorating disease conditions such as, but not limited to: dry rot; grey mold; *Rhizoctonia* disease; white mold; early blight; *phytophthora* blight of cucurbits; Northern leaf spot; and ear rot disease.

Kits

It is further envisioned that the methods and formulations described herein can be practiced through a kit or kits. A non-limiting example of such a kit comprises *Prunus maackii* materials (bark, plant tissues, or an extract) and one or more adjuvants in separate containers, where the containers may or may not be present in a combined configuration. Many other kits are possible, such as kits further comprising a spray bottle. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Examples

The following examples show the uniqueness of activity from *P. maackii* when compared with other *Prunus* species, as well as the biological activity against a range of fungal plant pathogens.

Figure 2A:
FIGS. 2A-2C: Photographs of crude extract collected from three different *Prunus* species: *P. maackii* (FIG. 2A), *P. serotina* (FIG. 2B), and *P. mahaleb* (FIG. 2C).
Figure 2B:
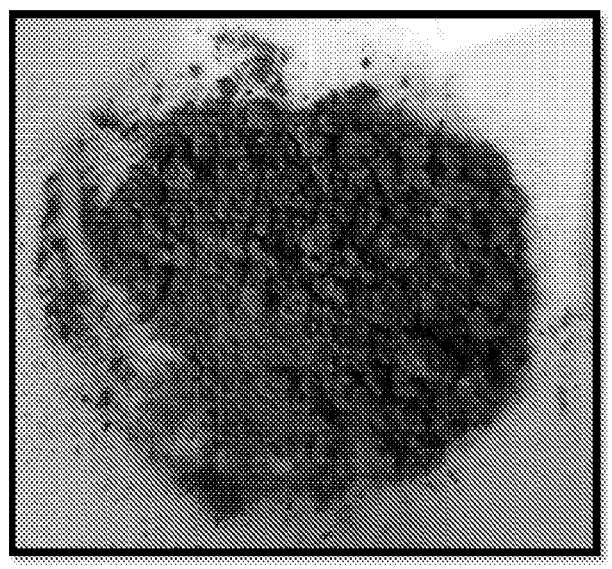
Figure 2C:
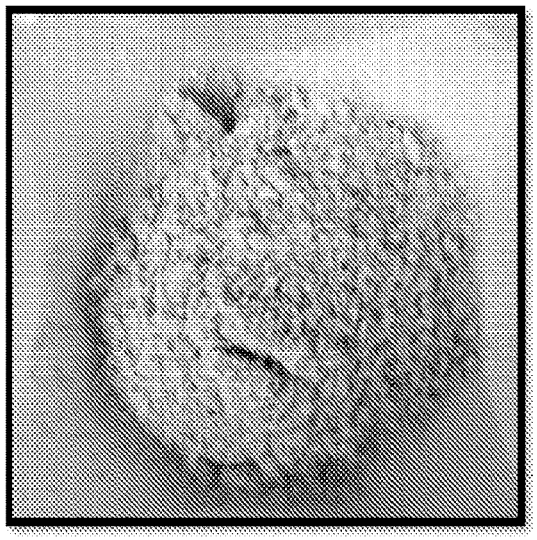

*P. maackii* extract was determined to be rich in phenolic compounds through the process illustrated in FIG. 1. Thin layer bioautography using 400 µg of plant material indicated that several antimicrobial compounds are present in the periderm. Crude extract was collected from 30 g of periderm tissues from each of three *Prunus* species: *P. maackii, P. serotina*, and *P. mahaleb*. (FIGS. 2A-2C.) These samples were extracted with 80% methanol. *Prunus maackii* (FIG. 2A) had over three times the amount of extract found in the periderm tissue as compared to *Prunus serotina* (FIG. 2B) and *Prunus mahaleb* (FIG. 2C). 4.5 g plus 2 g of crystallized *P. maackii* product were collected, compared to 1.92 g of *P. serotina* and 1.72 g of *P. mahaleb*.

Figure 3:
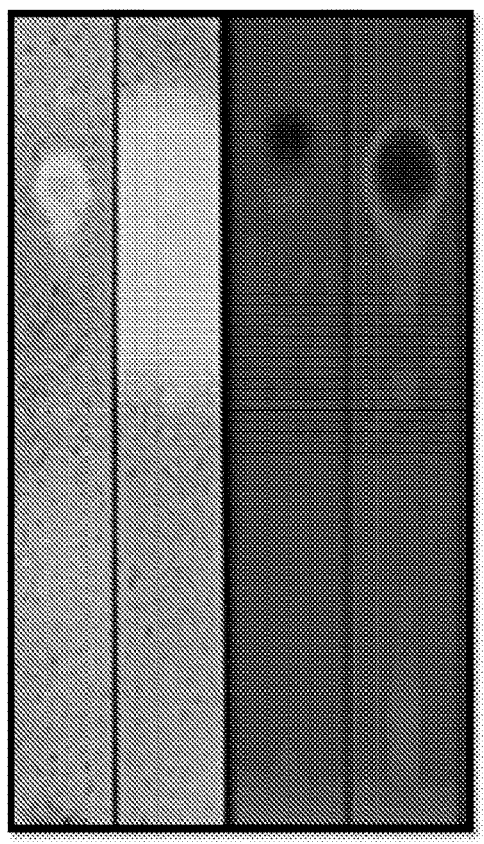
FIG. 3: Results of TLC bioassay of *P. maackii* crude extract. The white areas in the left two lanes are areas of antimicrobial activity (fungal inhibition). UV detection on TLC is seen in the right two lanes. From left to right, lanes 1 and 3 show alnusin, and lanes 2 and 4 show alnustinol.
Figure 20:
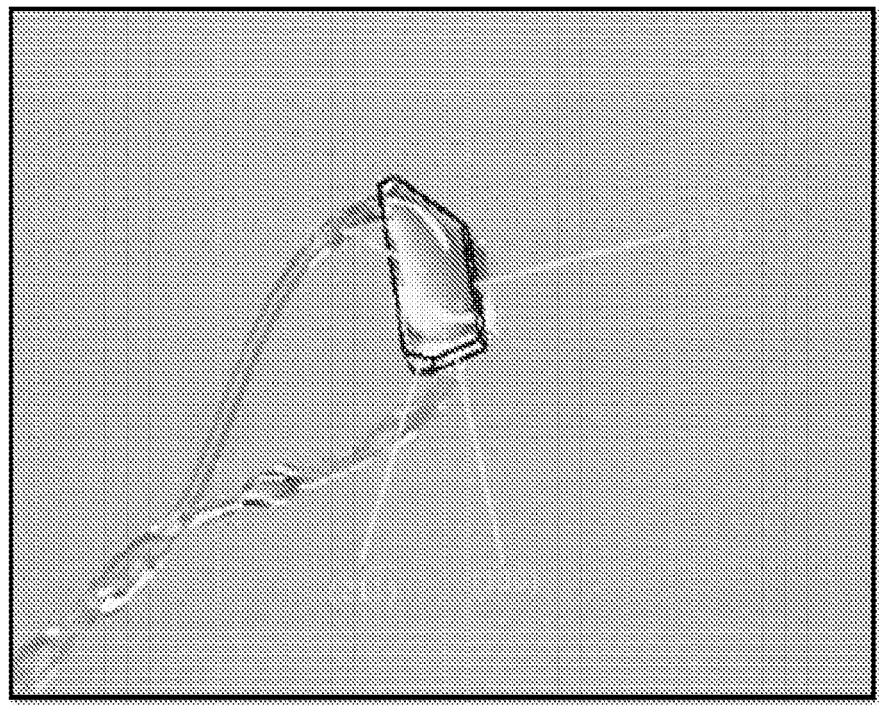
FIG. 20: Single crystal, selected from the crude crystal extract, used for X-ray crystallography.

FIG. 1 depicts the process of purification, X-ray crystallography, and TLC-bioassay conducted on the crystallized *P. maackii* product that resulted in identifying two antifungal flavonoids in the periderm. The TLC bioassay detected alnusin and alnustinol present in the extract. Results of the TLC assay are shown in FIG. 3. In FIG. 3, the white areas in the left two lanes are areas of fungal inhibition. UV detection on TLC is seen in the right two lanes. From left to right, lanes 1 and 3 show alnusin (3,5,6-trihydroxy-6-methoxyflavone), and lanes 2 and 4 show alnustinol (3,5,7-trihydroxy-6-methoxyflavanone). Notably, two stereoisomers of alnustinol were detected. After these compounds were identified, the structures were elucidated by X-ray crystallography. A photograph of a single crystal from the crude extract used for X-ray crystallography is shown in FIG. 20. The leaves of *Prunus maackii* were subjected to a similar process, resulting in the identification by X-ray crystallography of dihydrowogonin (5,7-dihydroxy-8-methoxyflavanone). Dihydrowogonin has antifungal activity. After the structures were identified, the isolated compounds were re-chromatographed and subjected to bioassays.

Figure 4:
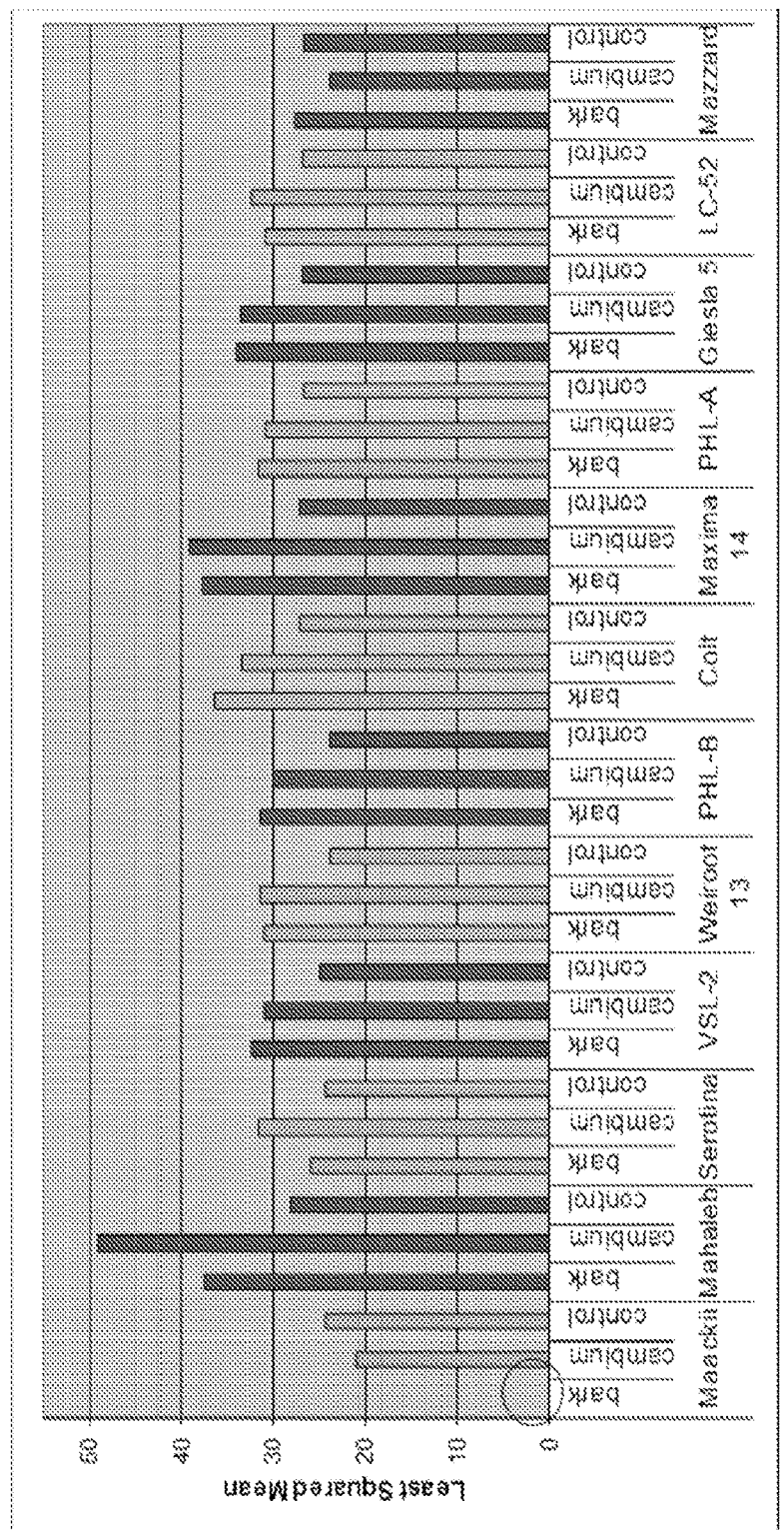
FIG. 4: Graph of screening results showing that the bark of *P. maackii* showed complete inhibition of *A. ostoyae*. Graph shows the growth of *A. ostoyae* on media incorporating periderm (12 grams periderm per liter). As seen in the graph, only *P. maackii* bark (periderm)-amended media completely inhibited growth (black circle on graph).

Table 1 lists the variety name and species names of *Prunus* species used for in vitro assays of tissues for antifungal activity. The periderm of *Prunus maackii* was found to inhibit the growth of a variety of Ascomycete, Basidiomycete, and Oomycete plant pathogens when incorporated into culture media at 0.6 mg/mL. The growth of *Armillaria ostoyae* on periderm-incorporated medium (PAM) from *P. maackii* at 12 g/l was completely inhibited. (FIG. 4) Periderm from other *Prunus* species did not inhibit fungi at similar or higher concentrations. (FIG. 4)

Figure 5A:
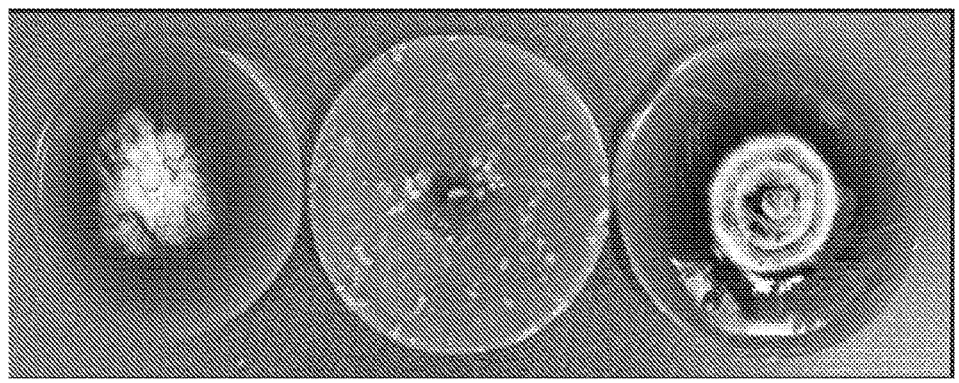
FIGS. 5A-5C: Photographs showing *Armillaria ostoyae* growth on growth media containing three types of tissues from *P. maackii* (FIG. 5A), *P. mahaleb* (FIG. 5B), and *P. serotina* (FIG. 5C). From left to right, the medium types are YMPG, periderm, and cambium. Only *P. maackii* periderm suppressed growth (FIG. 5A; middle).
Figure 5B:
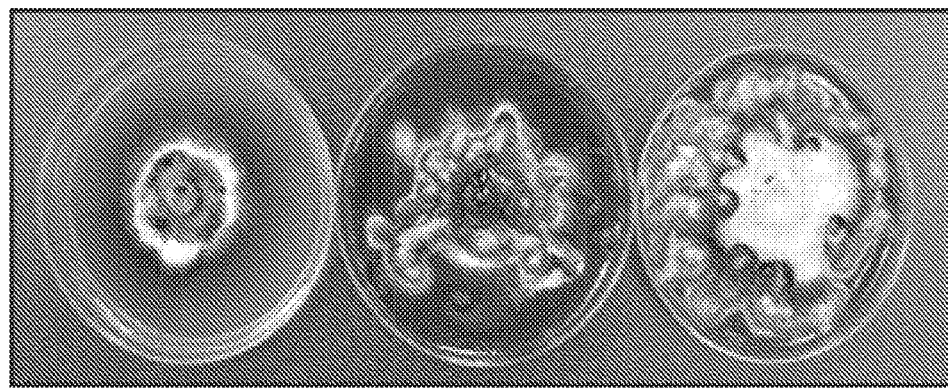
Figure 5C:
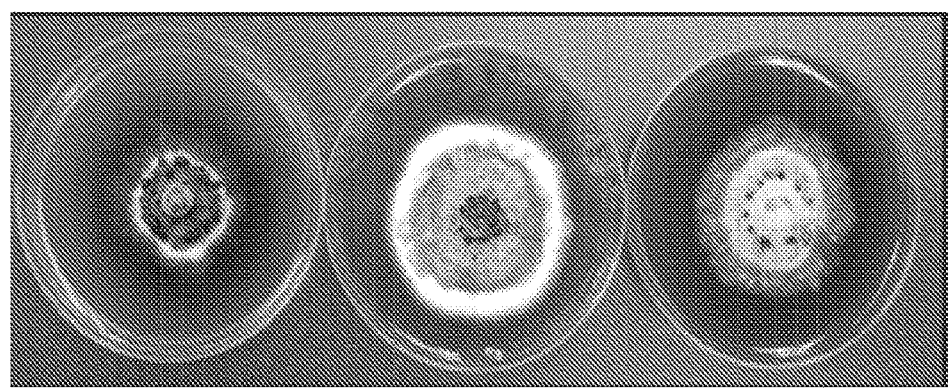
Figure 6:
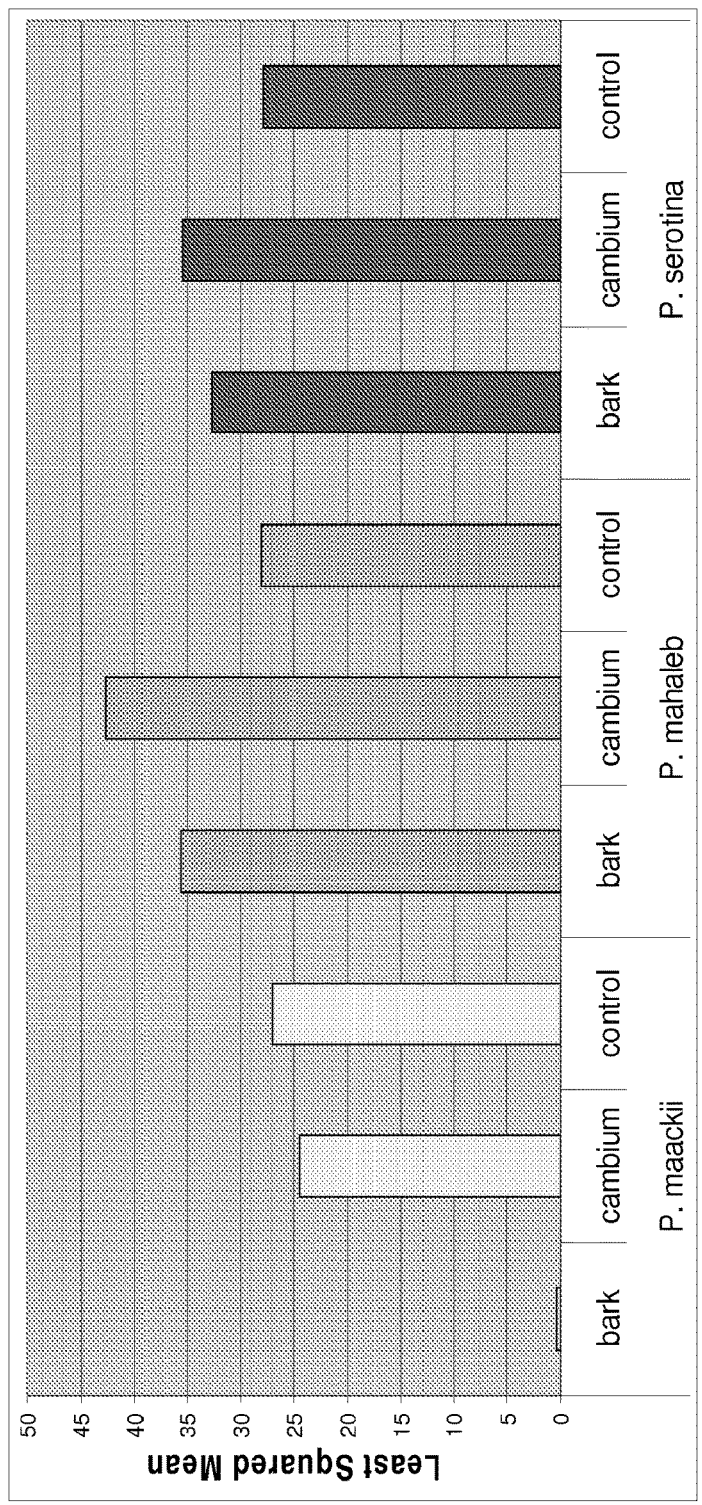
FIG. 6: Graph showing the growth of *A. ostoyae* on periderm and cambium tissues incorporated into media.
Figure 7:
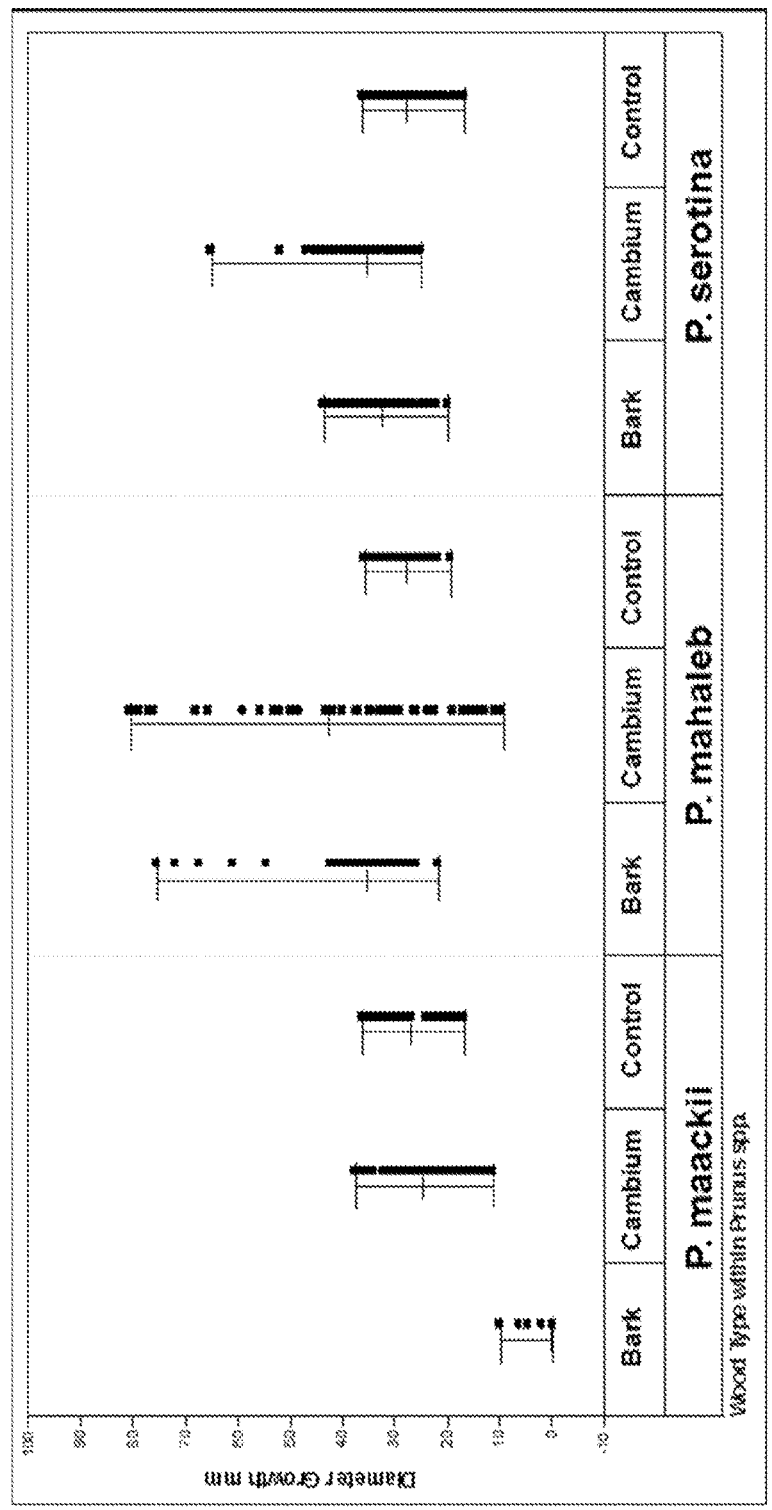
FIG. 7: Graph showing the variability of means in the diameter of the *A. ostoyae* growth shown in FIG. 4.
Figure 8A:
FIGS. 8A-8D: Periderm-amended medium (PAM) bioassay of *Prunus maackii* (FIG. 8A), *Prunus serotina* (FIG. 8B), *Prunus mahaleb* (FIG. 8C), and a control (FIG. 8D). Formation of crystals, which indicates concentrated antifungal compounds, only occurred on the surface of the PAM from *P. maackii*.
Figure 8B:
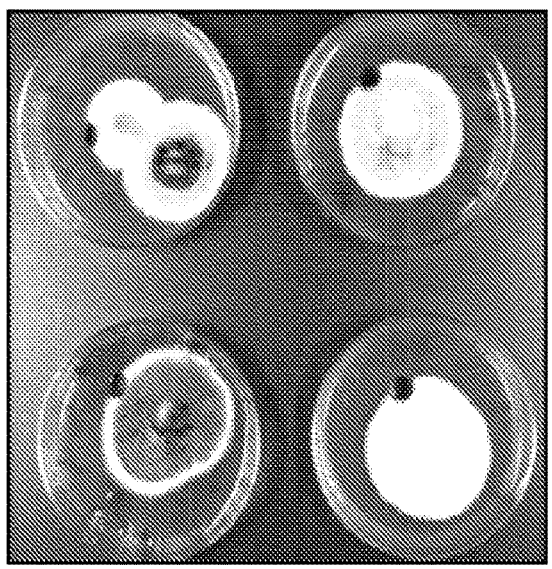
Figure 8C:
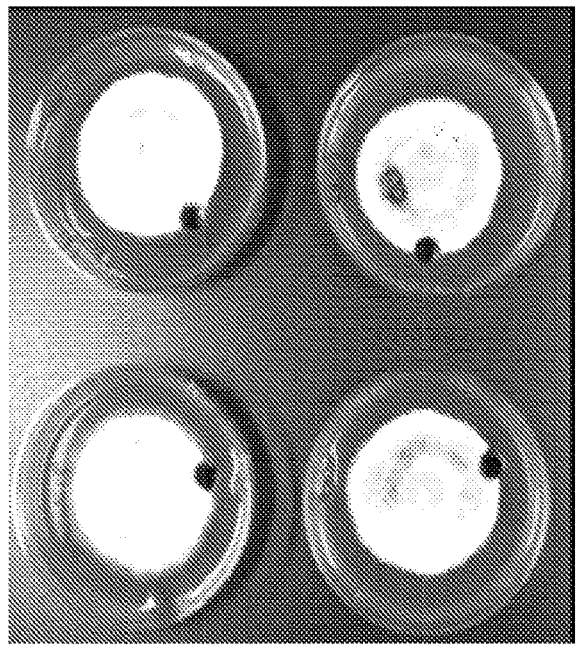
Figure 8D:
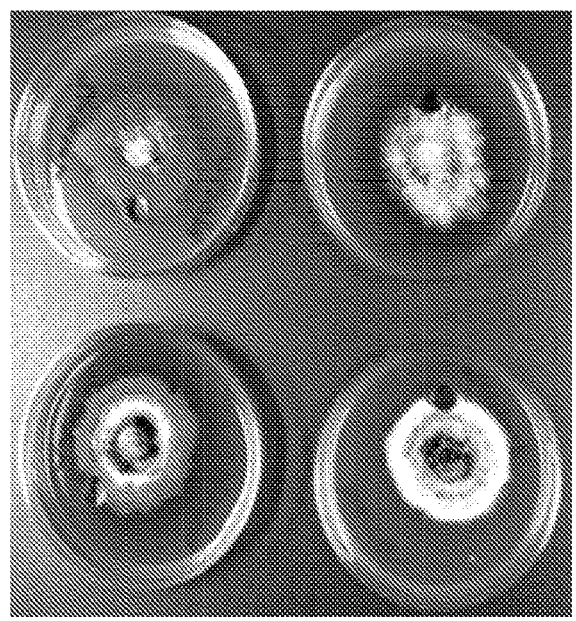
Figure 10:
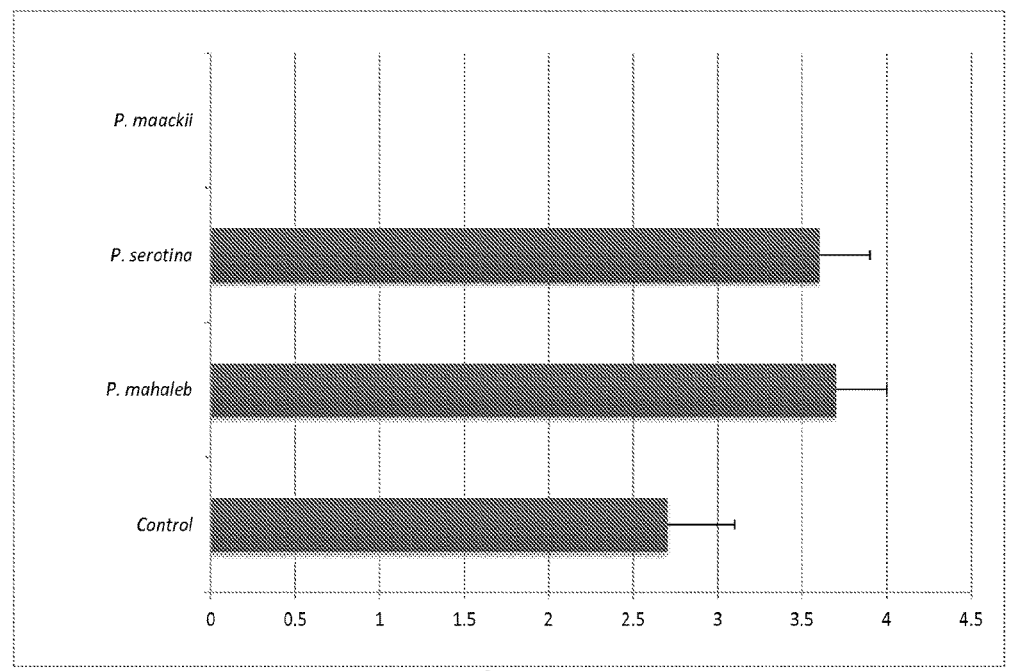
FIG. 10: Growth of *A. ostoyae*, inoculated on less than 24 hour-old PAM.

*A. ostoyae* growth in nutrient medium, periderm medium, and cambium medium was compared between *P. maackii, P. mahaleb*, and *P. serotina*. As seen from FIGS. 5-7, growth was inhibited by the periderm of *P. maackii*, and was not inhibited by the other *Prunus* species. As seen in FIG. 6, growth of *A. ostoyae* in the control medium was less than in the bark and cambium mediums of *P. mahaleb* and *P. serotina*, in contrast to the bark and cambium media from *P. maackii*. As seen in FIG. 10, the growth of *A. ostoyae* was completely inhibited when inoculated on less than 24 h old PAM.

A periderm-amended medium bioassay was conducted at a screening concentration of 12 mg/mL (3 g/250 mL). *P. maackii* was the only species found to be significantly different by Tukey's HSD test, p=0.05. (FIGS. 8A-8D.) The formation of crystals, which indicates the presence of concentrated antifungal compounds, only occurred on the surface of the Periderm-Amended Medium from *P. maackii*.

TABLE 1

Variety name and species name of several *Prunus* species used in an in vitro assay of tissues for antifungal activity.

| Variety Name | Species |
| --- | --- |
| Mazzard | *Prunus avium* |
| P-HL A | *P. avium × P. cerasus* |
| P-HL B | *P. avium × P. cerasus* |
| Colt | *P. avium × P. pseudocerasus* |
| Weiroot 13 | *P. cerasus* |
| Gisela ® 5 | *P. cerasus × P. canescens* |
| LC-52 | *P. cerasus × (P. cerasus × P. maacki)* |
| VSL-2 | *P. fruticosa × P. serrulata* |
| Maxma 14 | *P. mahaleb × P. avium* |
| Mahaleb | *P. mahaleb* |
| (*Maackii*) Amur Choke Cherry | *P. maackii* |
| Black Cherry | *P. serotina* |

Figure 9A:
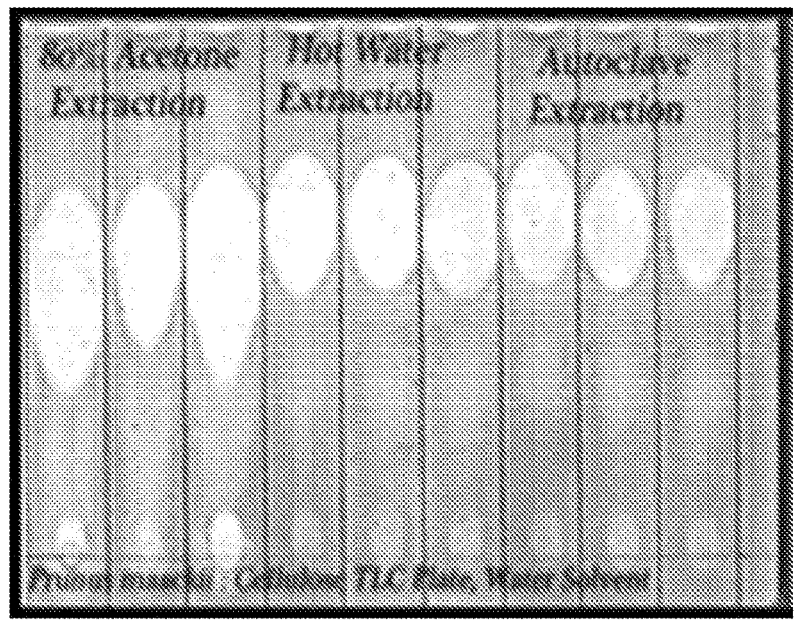
FIGS. 9A-9C: Photographs of TLC plates for three extraction types (from left to right: 80% acetone extraction, hot water extraction, and autoclave extraction) of three *Prunus* species: *Prunus maackii* (FIG. 9A), *Prunus serotina* (FIG. 9B), and *Prunus mahaleb* (FIG. 9C). The white areas on the plates indicate antifungal compounds.
Figure 9B:
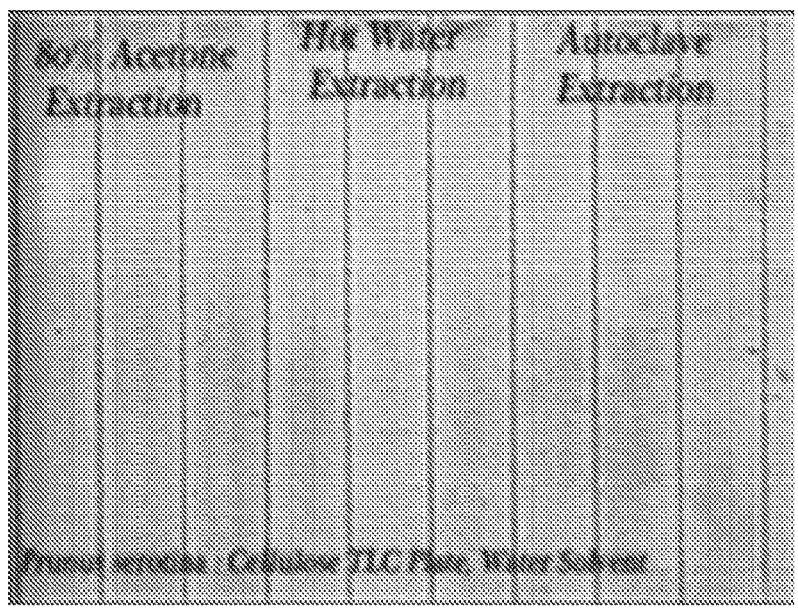
Figure 9C:
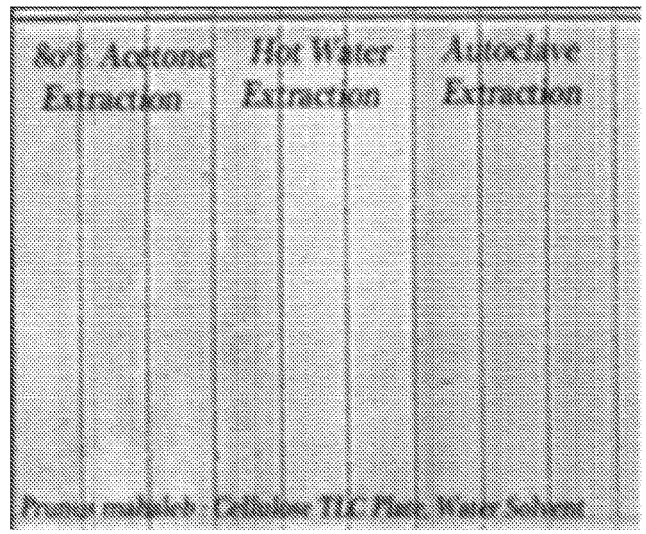

A TLC-bioassay of extract from *Prunus maackii, P. serotina*, and *P. mahelab* was conducted using three different extraction methods. Periderm tissue was extracted in 80% acetone, in hot water, or in water in an autoclave. Extracts were tested for antimicrobial activity by a thin layer chromatography bioassay on cellulose TLC plates. Samples were separated with, and the plates were developed in, water. Photographs of the TLC plates are shown in FIGS. 9A-9C. Antifungal activity is seen as a white area against a dark background of spores and mycelia of the test fungus *Cladosporium cucumerinum*. As seen from these photographs, only *P. maackii* contained significant antifungal activity. Several areas of antifungal activity were observed. Furthermore, this demonstrates that the antifungal activity of *P. maackii* is easily extracted and is heat-stable.

Figure 11:
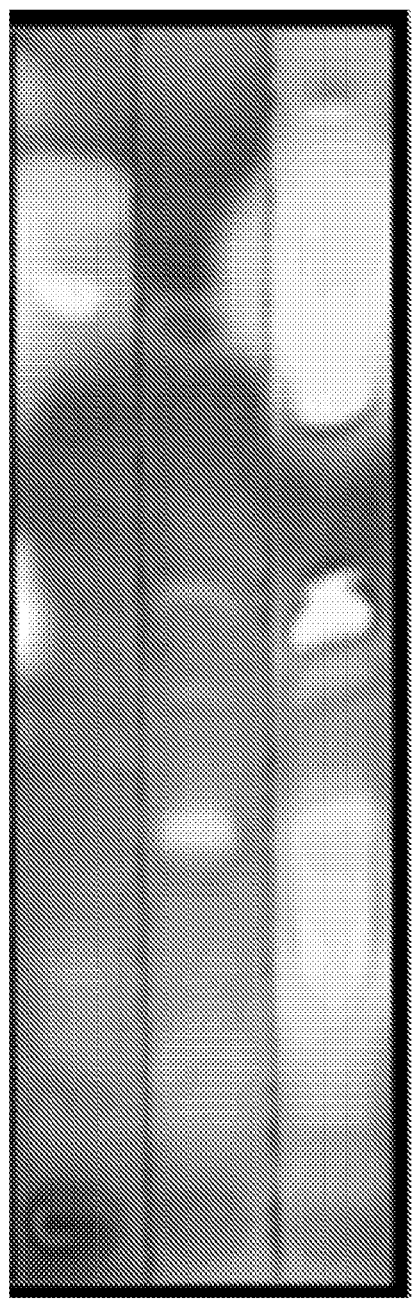
FIG. 11: Results of TLC bioassay of periderm extracts from three *Prunus* species. The left lane is *P. mahaleb*, the middle lane is *P. serotina*, and the right lane is *P. maackii*.

A TLC bioassay of periderm extracts from three *Prunus* species was conducted. Periderm tissues were extracted with 80% acetone. The results are shown in FIG. 11, where the left lane is *P. mahaleb*, the middle lane is *P. serotina*, and the right lane is *P. maackii*. Separation of periderm extracts on silica gel G was done using a chloroform:methanol mixture at 90/10 v/v. These results are in agreement with activity observed in the petri dish assays.

Figure 12:
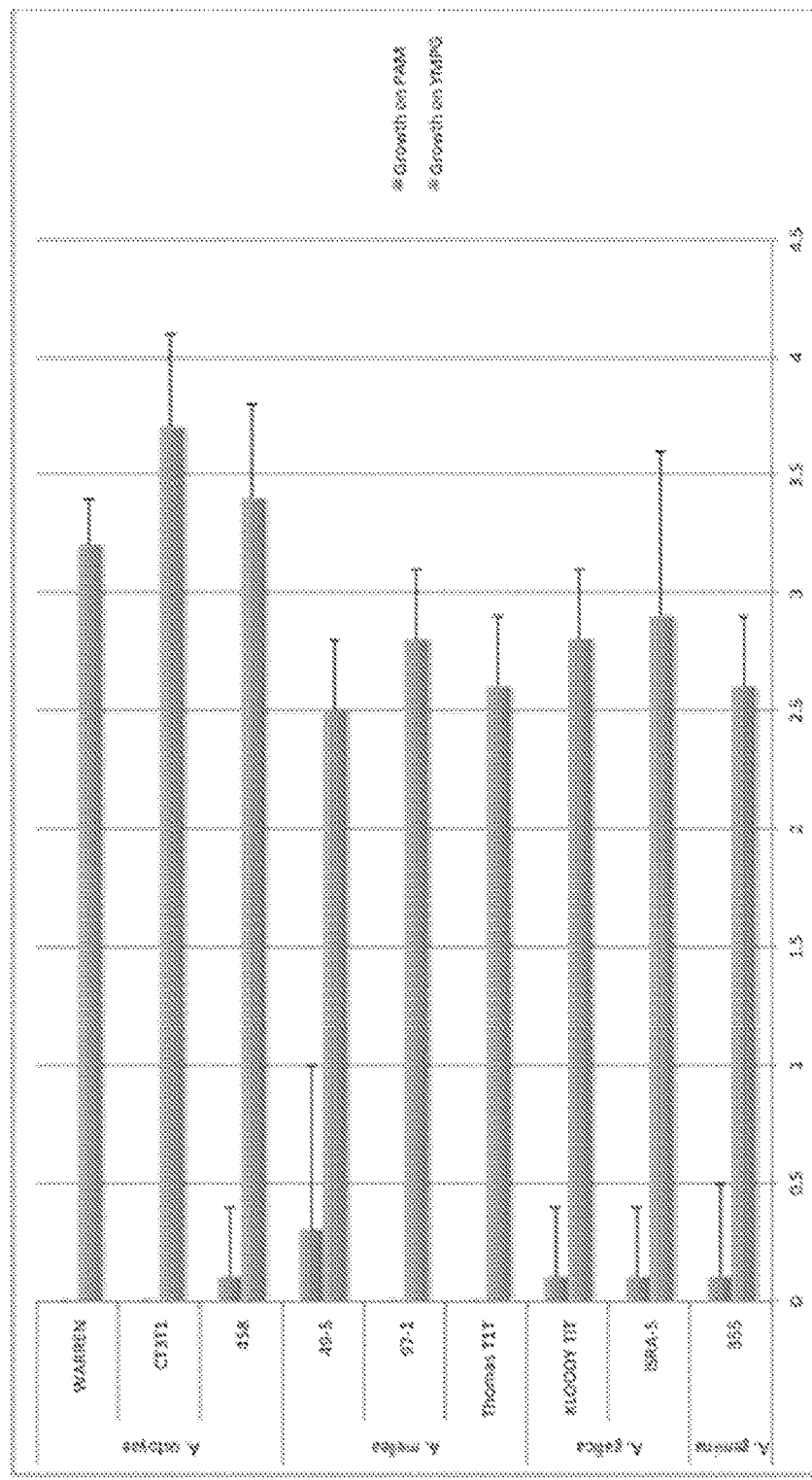
FIG. 12: Growth of 4 *Armillaria* species (9 isolates total) on periderm-amended medium from *P. maackii*. The x-axis is the diameter of colony growth.

The antifungal spectrum of the periderm of *P. maackii* was assayed by incorporating the periderm into culture media. A bioassay was conducted with 4 *Armillaria* species using 9 isolates in total at a concentration of 12 mg periderm per mL of media (3 g periderm/250 mL media). All 9 isolates were significantly inhibited when allowed to grow on periderm-amended medium from *P. maackii*. (FIG. 12) Table 2 lists the fungitoxicity and growth reduction of viable isolates. The fungitoxicity values are based on the number of mycelia plugs that failed to grow when transferred to nutrient medium (YMPG). The growth reduction is based on the viable (if any) mycelia plugs that were grown on PAM from *Prunus maackii* and then transferred to YMPG medium.

TABLE 2

PAM toxicity bioassay results with 4 *Armillaria* speciecs, 9 isolates total. The average fungitoxicity and growth reduction of isolates that were grown on *Prunus maackii* periderm-amended medium (PAM) when transferred to YMPG nutrient medium are shown.

| Species | Isolate ID | Fungitoxicity (%) | Growth Reduction (%) of viable isolates |
| --- | --- | --- | --- |
| *A. gemina* | 35-5 | 78 | 90 |
| *A. gallica* | ISRA-5 | 24 | 97 |
|  | Kloody TIT | 74 | 95 |

TABLE 2-continued

PAM toxicity bioassay results with 4 *Armillaria* species, 9 isolates total. The average fungitoxicity and growth reduction of isolates that were grown on *Prunus maackii* periderm-amended medium (PAM) when transferred to YMPG nutrient medium are shown.

| Species | Isolate ID | Fungitoxicity (%) | Growth Reduction (%) of viable isolates |
|---|---|---|---|
| *A. mellea* | Thomas T1T | 50 | 90 |
| | Van Buren Co. | | |
| | 97-1 | 100 | 0 (non-viable) |
| | 49-5 | 28 | 92 |
| *A. ostoyae* | 4-58 | 100 | 0 (non-viable) |
| | CT3T1 | 80 | 98 |
| | Warren | 94 | 79 |

Figure 13:
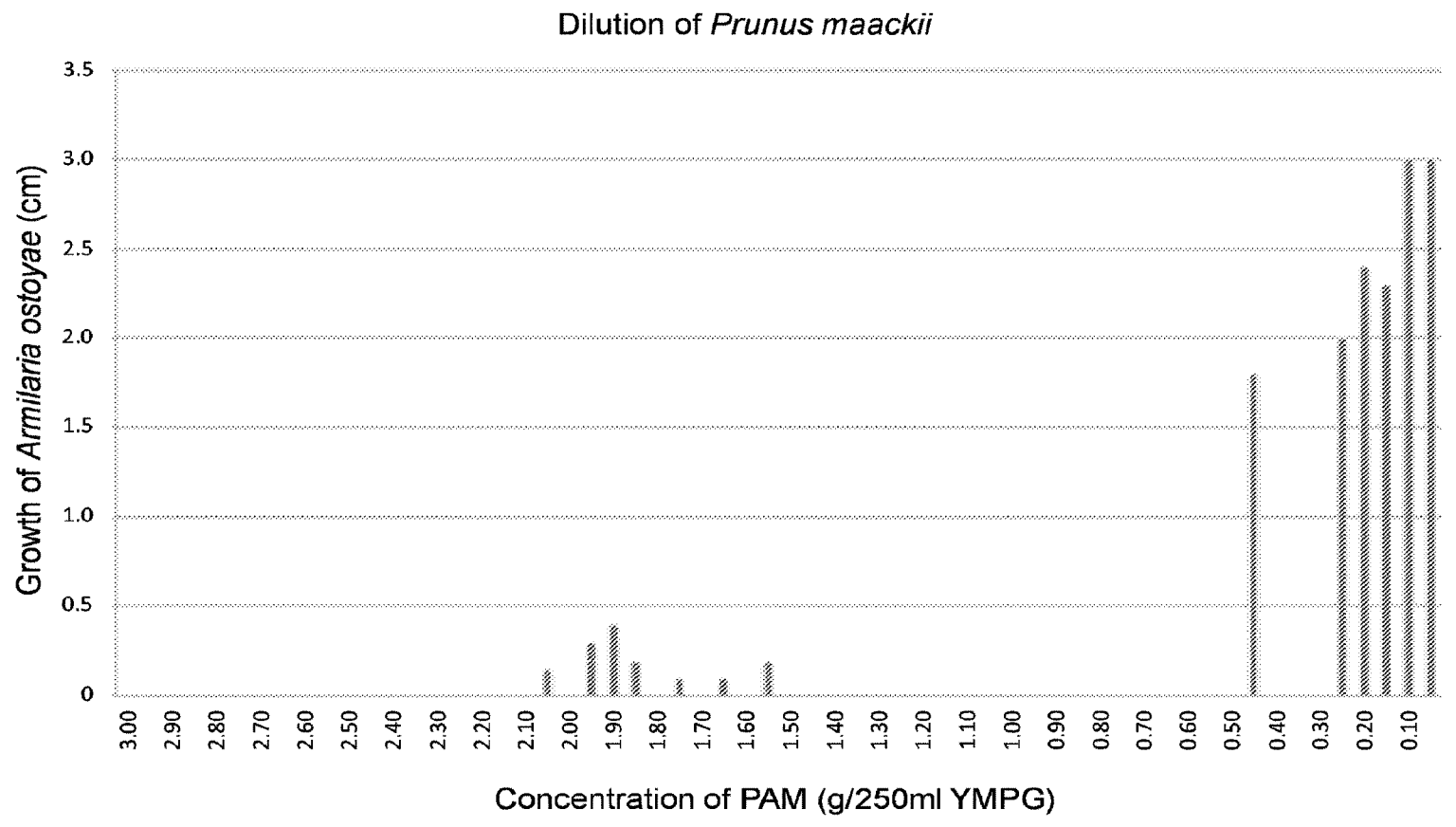

A concentration gradient evaluation of *Prunus maackii* periderm tissue was conducted for the identification of the antimicrobial threshold. 3 g of periderm tissue per 250 mL of YMPG was used as the screening concentration, and YMPG alone was used as a control. The results are shown in FIG. 13 and Table 3. Without wishing to be bound by theory, it is believed the extreme outliers seen on the graph in FIG. 13 are due to hydrogen bonding of antifungal compounds, which causes a slight decrease in strength of antimicrobial activity. Table 3, lists the average radial growth and average viability percentage at concentrations categorized into increments of 0.50 g, based on the data shown in FIG. 13. The average radial growth is the growth of *A. ostoyae* (Warren isolate) on the periderm-amended medium from *P. maackii*. The average viability percentage (%) refers to growth of *A. ostoyae* on periderm-amended media/growth on YMPG×100. The most virulent *Armillaria* species (*A. ostoyae*; Warren isolate) was used for the inoculation of petri dishes that contained PAM (15 dishes/concentration).

TABLE 3

Average radial growth and average viability percentage at concentrations categorized into increments of 0.50 g, based on the data shown in FIG. 13. The average radial growth is the growth of *A. ostoyae* (Warren isolate) on the PAM from *P. maackii*. The average viability percentage (%) refers to growth of *A. ostoyae* on PAM/Growth on YMPG × 100.

| Concentration of PAM (g/250 ml YMPG) | Average Radial Growth (cm) | Average Viability Percentage (%) |
|---|---|---|
| 3.00-2.50 | <0.50 | 30 |
| 2.45-2.00 | <0.50 | 25 |
| 1.95-1.50 | <0.50 | 57 |
| 1.45-1.00 | <0.50 | 47 |
| 0.95-0.65 | <0.50 | 95 |
| 0.60-0.15 | <2.50 | 100 |
| 0.10-0.05 | < or =3.00 | 100 |
| Control (0.00) | 3.2 | 100 |

Figure 14:
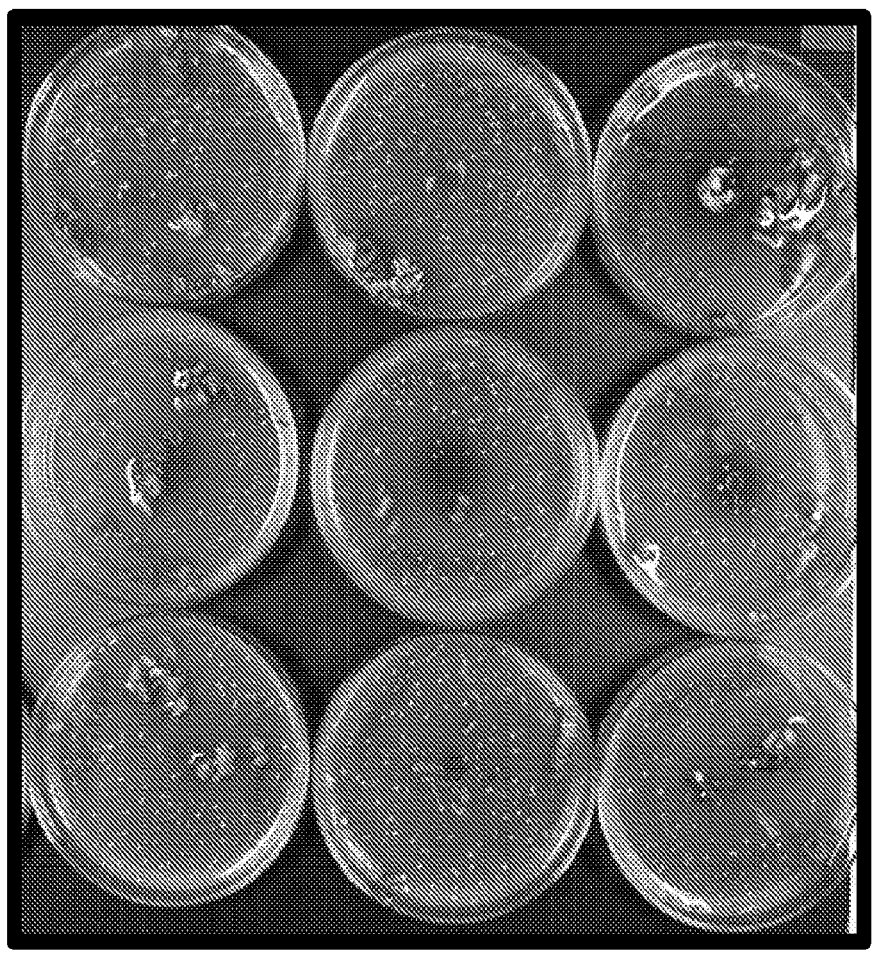
FIG. 14: Results of toxicity evaluation.

The toxicity of *Prunus maackii* was evaluated. Compounds from the periderm of *Prunus maackii* precipitate were evaluated over time in the culture medium. The results are shown in FIG. 14. Antifungal compounds crystallize out of the PAM, which results in a slight decrease in toxicity. Formation of crystals on the surface of the medium was only observed in *Prunus maackii*. The PAM was used within 24 hours of preparation.

Figure 15:
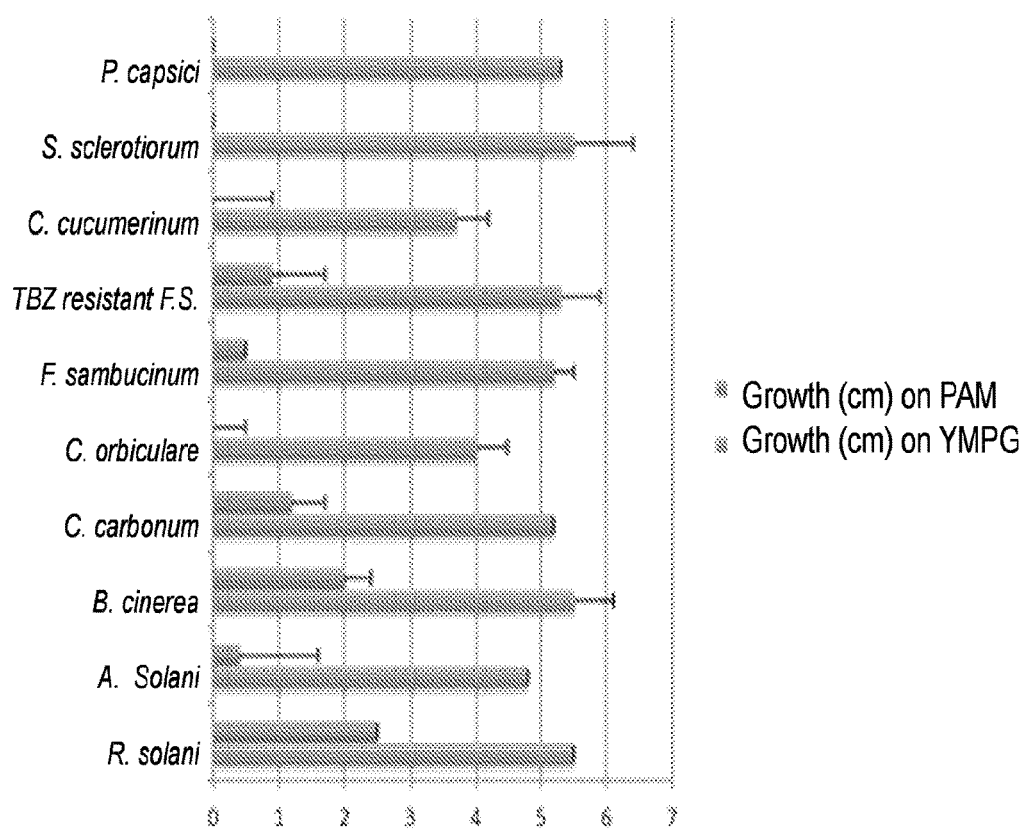
FIG. 15: Growth of fungi non-pathogenic to *P. maackii* on YMPG and PAM from *P. maackii*. "TBZ Resistant F. S." refers to Thiabendazole-resistant *F. sambucinum*.

Fungi that are non-pathogenic to *Prunus maackii* were grown in YMPG and PAM. A graph depicting the growth of these fungi is shown in FIG. 15. 5.5 cm is the maximum radial growth in the small petri dish that was used. Fast-growing species often grew to the edge of the petri dish. Photographs showing the actual growth of these fungi are shown in FIGS. 16A-16J.

*Phytophthora capsici* (FIG. 16J) is one of the most serious threats to the production of cucurbits and peppers worldwide, and is resistant to some fungicides. Its hosts include cucurbits (cantaloupe, cucumber, gourd, honeydew, pumpkin, squash, watermelon), eggplant, peppers, tomatoes, and several other vegetable and weed species. *P. capsici* causes a disease known as *phytophthora* blight of cucurbits. Recently, this disease has increased dramatically in certain cucurbit-growing areas in the world, causing up to 100% yield loss. Cucurbit industries have been seriously threatened by heavy crop losses due to this pathogen. As seen from FIG. 16J, PAM from *P. maackii* completely inhibited the growth of *Phytophthora capsici*.

Figure 16A:
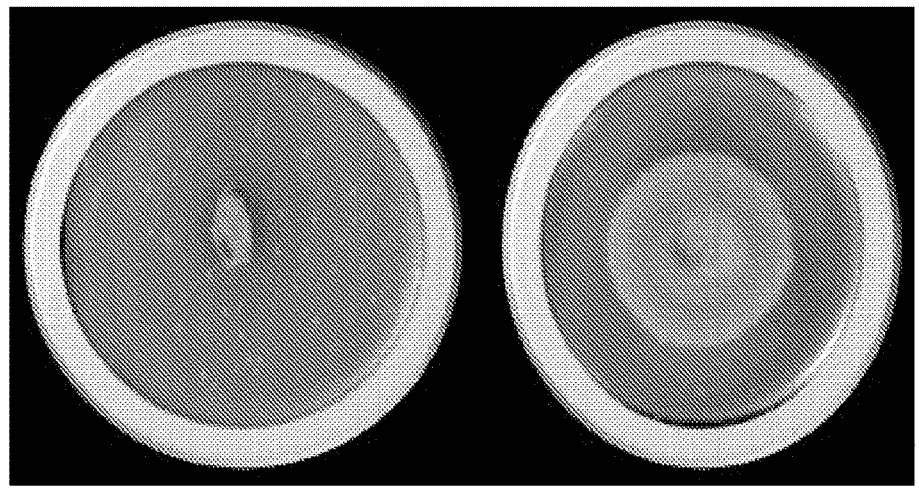
FIGS. 16A-16J: Photographs showing the actual growth of the fungi of FIG. 15.
Figure 16B:
Figure 16C:
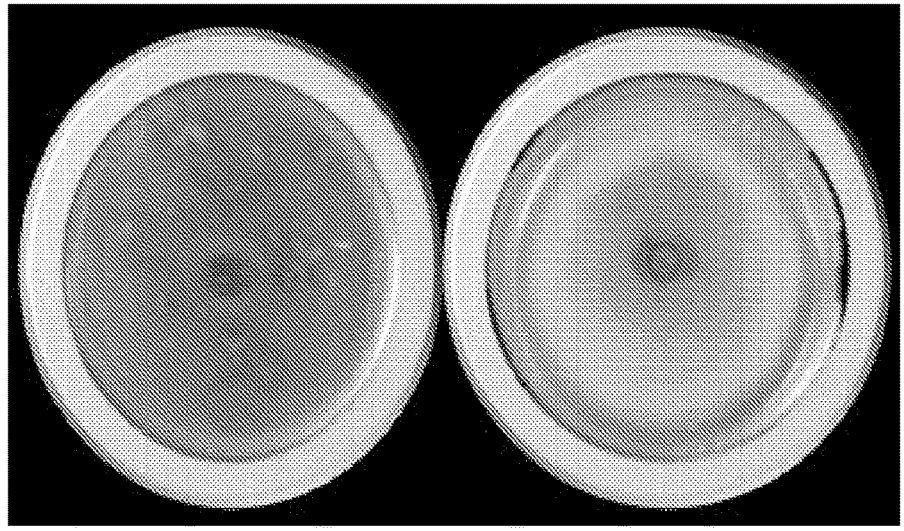
Figure 16D:
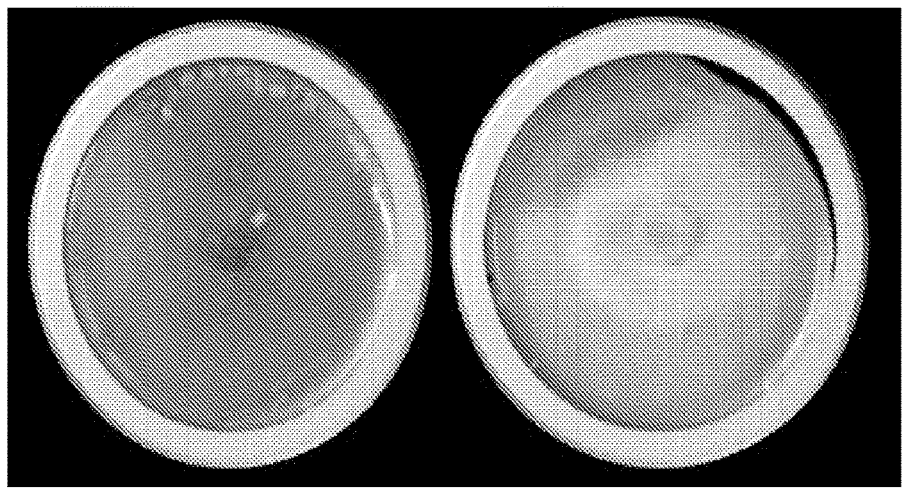
Figure 16E:
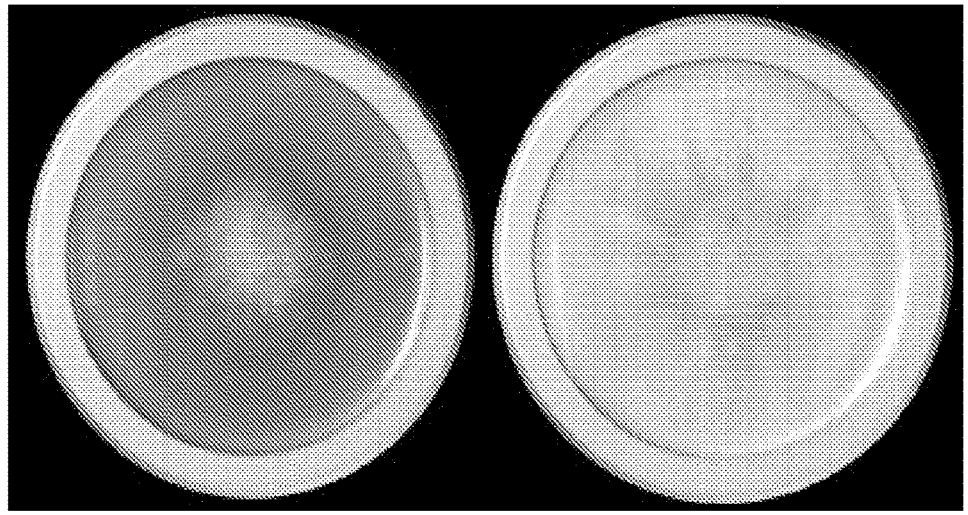
Figure 16F:
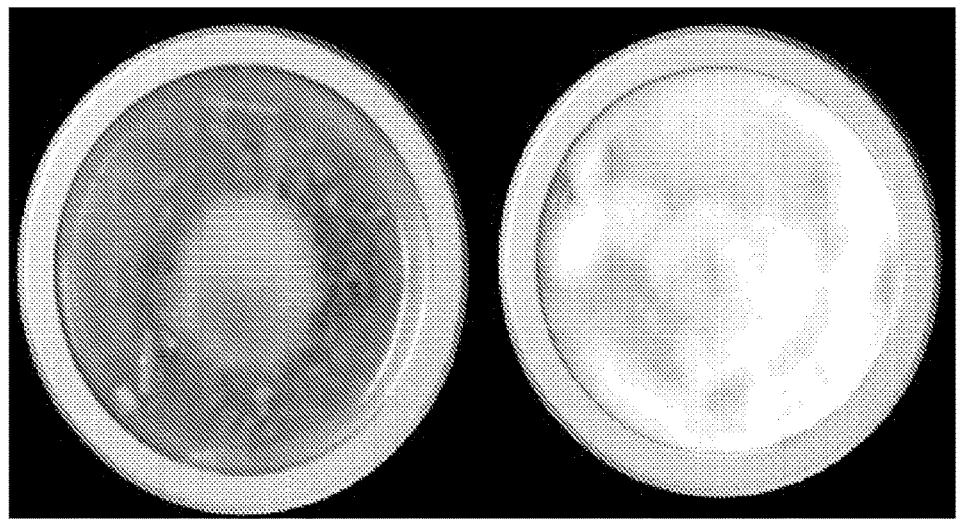
Figure 16G:
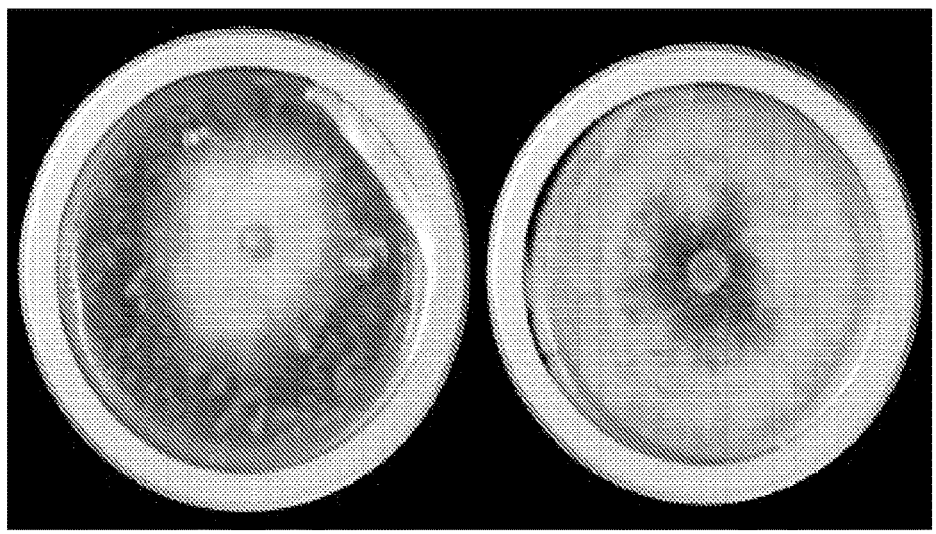
Figure 16H:
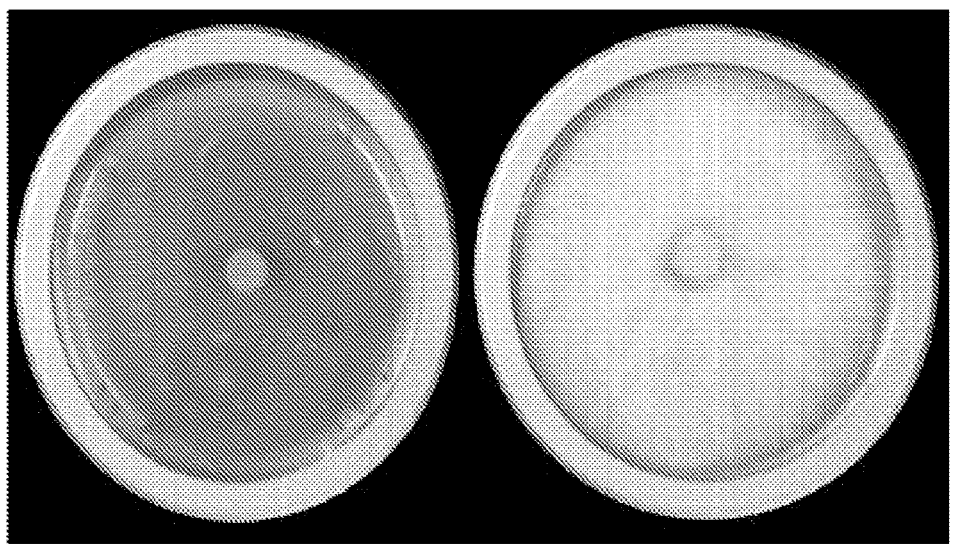
Figure 16I:
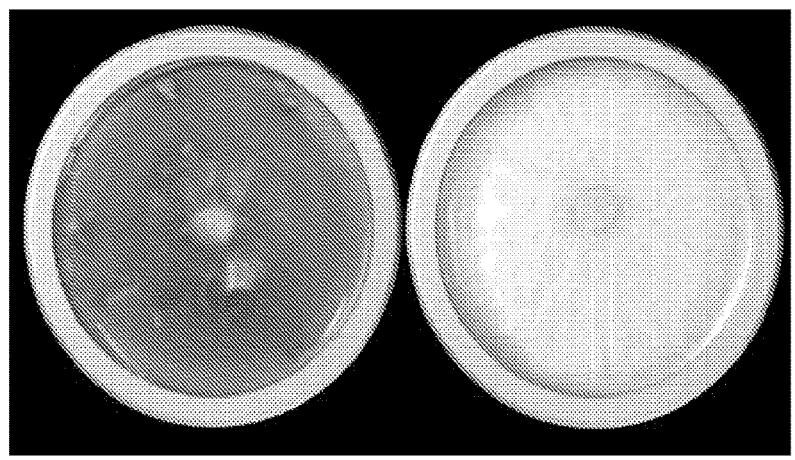
Figure 16J:
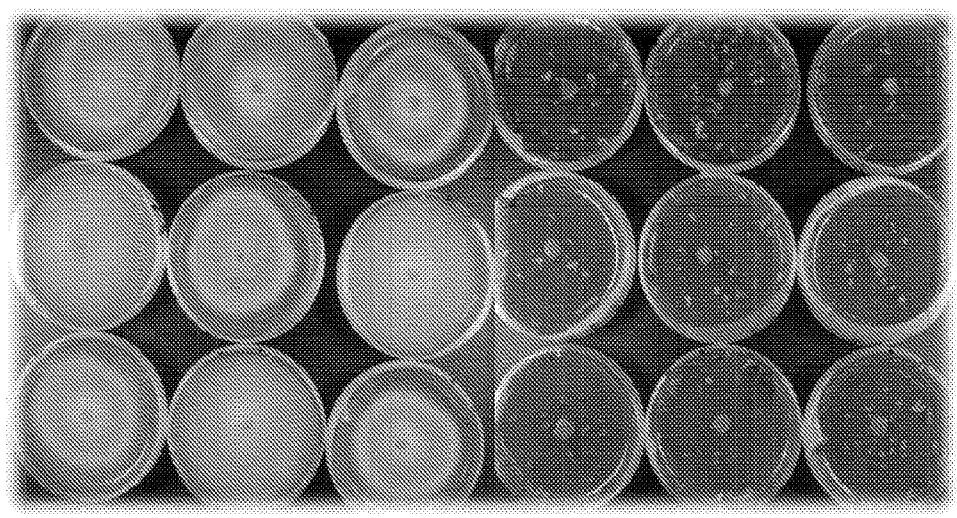

*Sclerotinia sclerotiorum* (FIG. 16B), which causes white mold, is hosted by legumes, sunflowers, most vegetables, tobacco, many flowering bedding plants, and stone fruits. *Sclerotinia* can normally survive and remain infective for up to 5 years. Literature reports of crop losses due to *Sclerotinia sclerotiorum* range from negligible to 100%. Crops where average annual losses from this disease are thought to exceed 1% include bean, eggplant, lettuce, peanut, potato, soybean, and sunflower. Many of the greatest losses occur in intensive cropping environments. *Sclerotinia sclerotiorum* was inhibited by *P. maackii*. (FIG. 16B)

Extracts from the periderm of *P. maackii* were also able to completely inhibit *Fusarium sambucinum* (FIG. 16H) and Thiabendazole (TBZ) resistant *F. sambucinum* (FIG. 16I), which are responsible for dry rot of potato around the world. Dry rot of potato is an important storage and seed piece decay pathogen. Overcoming this pathogen's resistance to synthetic fungicides is a long-felt need in the agriculture industry.

Figure 17:
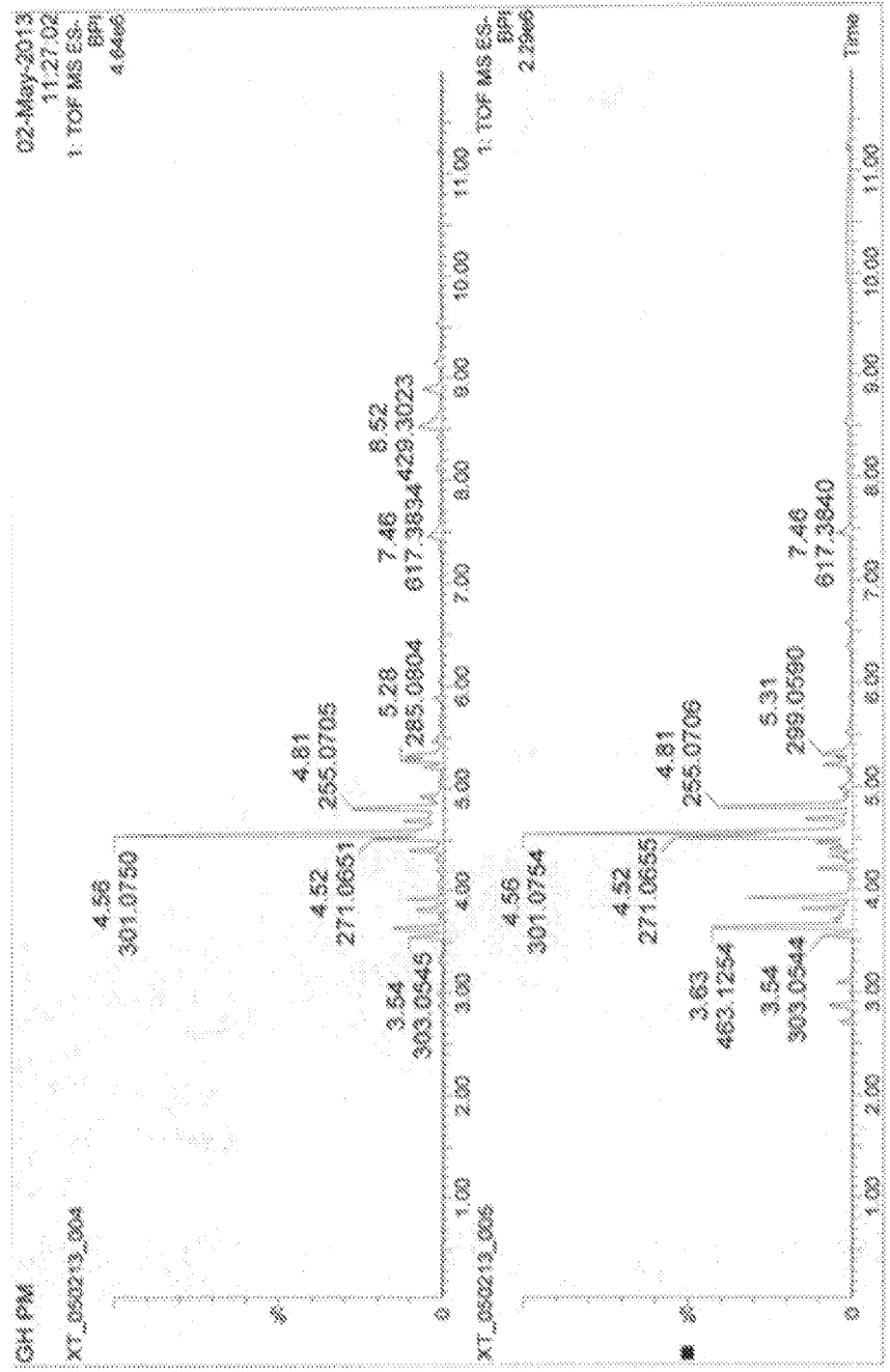
FIG. 17: Results of HPLC-MS analyses of periderm tissue from both young (bottom) and mature (top) *P. maackii*.

HPLC-MS analyses of the chemical contents in the periderm tissue from both young and mature *P. maackii* were conducted. The results are shown in FIG. 17. As seen in FIG. 17, the same compounds were found in both tissues. The peak in each spectrum around 271 g/mol is attributed to naringenin or naringenin chalcone. Without wishing to be bound by theory, the peak around 255 g/mol is believed to be pinocembrin, which has antifungal activity.

Figure 19A:
FIGS. 19A-19D: Photographs of *Alternaria solani* (FIG. 19A), *Colletotrichum orbiculare* (FIG. 19B), *Cladosporium cucumerinum* (FIG. 19C), and *Cochliobolus carbonum* (FIG. 19D) in mulch-amended medium. *P. maackii* completely inhibited growth of all four of these pathogens.
Figure 19B:
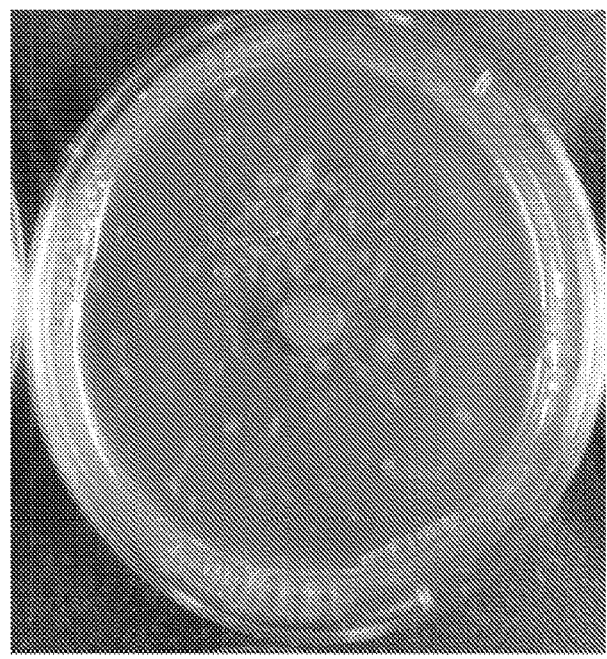
Figure 19C:
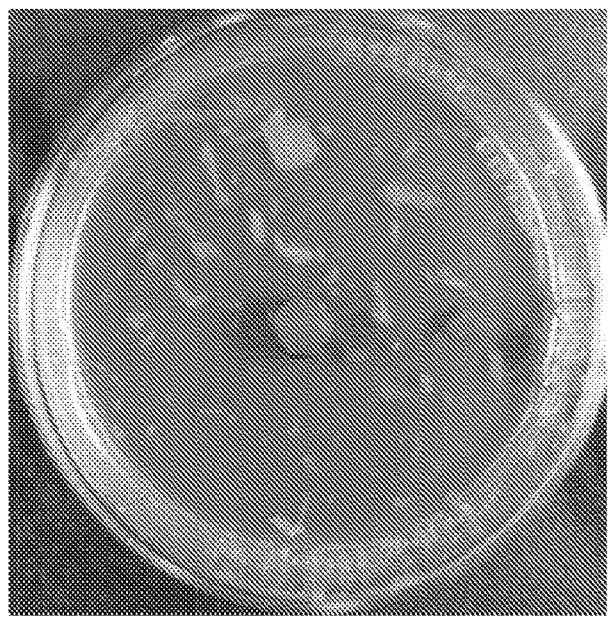
Figure 19D:
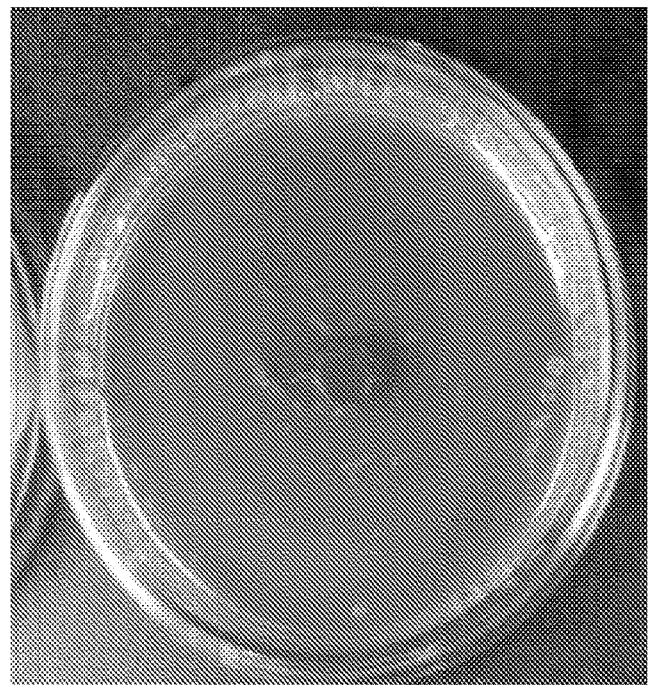

A wood mulch-amended medium was created using a screening concentration of 3 g/250 mL. The mulch was prepared by chipping whole twigs and branches. The medium contained mostly woody tissue (sapwood, where sap flows, and heartwood, where sap does not flow) (FIG. 18A), with very little periderm. The roots and shoots were determined to have many of the same compounds. (FIG. 18B.) However, the woody tissue was determined to have different chemistries than the periderm. Though the mulch extracts contain different chemistries than the other tissues in *P. maackii*, they are nonetheless potent pathogen inhibitors. At 3 g/250 mL (1.2%), the mulch extracts completely inhibited not only *Armillaria ostoyae*, but also *Alternaria Solani* (FIG. 19A), *Colletotrichum orbiculare* (FIG. 19B), *Cladosporium cucumerinum* (FIG. 19C), and *Cochliobolus carbonum* (FIG. 19D). *Alternaria Solani* causes a disease known as early blight to vegetables such as tomatoes and potatoes. *Colletotrichum orbiculare* is a fungal pathogen that commonly affects melons and cucumbers. *Cladosporium cucumerinum* is a fungal pathogen that affects cucumbers. *Cochliobolus carbonum* is a species of filamentous ascomycetes that causes Northern leaf spot, ear rot disease, and *Helminthosporium* corn leaf spot. Thus, mulch extracts of *P. maackii* are also suitable for a wide variety of pathogen-inhibiting applications. For example, the mulch is suitable for use as a soil amendment to reduce risk of soil borne diseases. The entire *Prunus maackii* tree is valuable, possessing strong antimicrobial properties.

Materials and Methods

Mature *Prunus maackii* branches (about 2 cm in diameter) were collected at the NW Michigan Horticulture Research Station near Traverse City, Mich., and were stored at −20° C. until used for analysis. The periderm was removed from the branches and macerated with a razor blade.

For periderm-amended medium, periderm tissue was added to the liquid YMPG medium, prior to autoclaving, for a final concentration of 3 g of tissue per 250 mL of YMPG (1.2%). This bioassay was used for screening *Armillaria* species in addition to non-*Prunus* pathogens.

For tissue extraction for chemical analyses, 30 g of macerated periderm tissue was placed in 500 mL of 80% acetone. This tissue was allowed to extract for three days at room temperature. After the initial extraction, the tissue was rinsed twice with 100 mL of 100% acetone. All of the acetone extracts for each sample were combined and concentrated to near dryness by rotary evaporation at 37° C. As the extract was concentrated to reduce volumes of solvent, using the rotary evaporator, spontaneous crystallization occurred. After the crystal products were filtered out, the samples were concentrated to complete dryness by lyophilization. After lyophilization, the samples contained a dry powder extract that contained various sized crystals. The crystals were used for separation of compounds by dry column chromatography. The formation of single crystals allowed for X-ray crystallography.

For dry column chromatography, 3 g of crude crystal extract were dissolved in methanol and applied to the silica gel column. A hand-held UV light was used to detect and locate the different compounds in the column. Methanol was used to elute compounds from the silica gel. After elution of compounds from the silica gel, each fraction was evaporated to dryness in a scintillation vial and then dissolved in 1 mL of dichloromethane. One drop of toluene was added to each vile prior to capping the vial. Crystals were formed after 3 days of slow-evaporation on the laboratory bench.

For the TLC bioassay for the detection of antimicrobial activity, 5 μL of the samples (column fractions, suspended in 80% methanol) were applied to Analtech® silica gel (TLC) plates and were developed in a TLC tank (30×20×10 cm) using 100 mL of chloroform:methanol (8.5:1, v/v). Within 24 hours of developing the TLC plates, the plates were evenly sprayed with a dense fungal suspension of *C. cucumerinum* in ½ strength potato-dextrose broth and then placed in a moist incubation chamber for three days to allow fungal growth.

Certain embodiments of the methods and formulations disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the formulations and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of protecting a plant from a fungus or fungus-like pathogen, the method comprising applying an effective amount of a *Prunus Maackii* extract to a plant in need thereof, wherein the extract is obtained from *Prunus maackii* periderm and/or cambium tissue, and wherein the extract comprises 3, 5, 7-trihydroxy-6-methoxyflavone, 3,5,7-trihydroxy-6-methoxyflavanone, and/or 5,7-dihydroxy-8-methoxyflavonone.

2. The method of claim 1, wherein the pathogen is selected from the group consisting of an Ascomycete plant pathogen, a Basidiomycete plant pathogen, and an Oomycete plant pathogen.

3. The method of claim 1, wherein the fungus or fungus-like microorganism is selected from the group consisting of: *Sclerotinia sclerotiorum; Alternaria Solani; Armdlaria ostoyae*; other *Armillaria spp.; Colletotrichum orbiculare; Cladosporium cucumerinum; Cochliobolus carbonum; Fusarium sambucinum*; TBZ-resistant *F. sambucinum*; and *Phytophthora caspscici.*

4. The method of claim 1, wherein the extract is formulated as an aqueous solution further comprising one or more adjuvants.

5. The method of claim 1, wherein the extract is prepared by acetone extraction, hot water extraction, or autoclave extraction.

* * * * *